(12) United States Patent
Ng et al.

(10) Patent No.: US 10,524,679 B2
(45) Date of Patent: Jan. 7, 2020

(54) SYSTEM AND METHOD FOR DETERMINING ELECTROGRAM MORPHOLOGY RECURRENCE PATTERNS AND RATES DURING ATRIAL FIBRILLATION

(71) Applicant: Northwestern University, Evanston, IL (US)

(72) Inventors: Jason Ng, Evanston, IL (US); Jeffrey J. Goldberger, Skokie, IL (US); David Gordon, Chicago, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 15/034,296

(22) PCT Filed: Nov. 4, 2014

(86) PCT No.: PCT/US2014/063819
§ 371 (c)(1),
(2) Date: May 4, 2016

(87) PCT Pub. No.: WO2015/066678
PCT Pub. Date: May 7, 2015

(65) Prior Publication Data
US 2016/0262643 A1 Sep. 15, 2016

Related U.S. Application Data

(60) Provisional application No. 61/899,453, filed on Nov. 4, 2013.

(51) Int. Cl.
*A61B 5/046* (2006.01)
*A61B 5/04* (2006.01)
(Continued)

(52) U.S. Cl.
CPC .......... *A61B 5/046* (2013.01); *A61B 5/04012* (2013.01); *A61B 5/7246* (2013.01);
(Continued)

(58) Field of Classification Search
CPC ... A61B 5/024; A61B 5/02405; A61B 5/0245; A61B 5/04012; A61B 5/0402;
(Continued)

(56) References Cited

U.S. PATENT DOCUMENTS 7,412,282 B2   8/2008  Houben
8,535,301 B2   9/2013  Cox et al.
(Continued)

FOREIGN PATENT DOCUMENTS

WO   2010054409 A1   5/2010
WO   2012149128 A1   11/2012

OTHER PUBLICATIONS

Lin et al. "Prevalence, Characteristics, Mapping, and Catheter Ablation of Potential Rotors in Nonparoxysmal Atrial Fibrillation". Circulation: Arrhythmia and Electrophysiology. 2013;6:851-858, originally published Oct. 15, 2013.*
(Continued)

*Primary Examiner* — Eugene T Wu
(74) *Attorney, Agent, or Firm* — Quarles & Brady LLP; Jonathan Stone

(57) ABSTRACT

At least one location of interest for perpetuation or persistence of arrhythmia or atrial fibrillation is identified by determining a repeatability of electrogram morphologies from electrical recordings within at least one atrium.

24 Claims, 16 Drawing Sheets

(51) Int. Cl.
*A61B 5/00* (2006.01)
*A61B 5/044* (2006.01)
*A61B 18/14* (2006.01)
*A61B 18/00* (2006.01)

(52) U.S. Cl.
CPC ........... *A61B 5/044* (2013.01); *A61B 18/1492* (2013.01); *A61B 2018/00375* (2013.01); *A61B 2018/00577* (2013.01); *A61B 2018/00839* (2013.01); *A61B 2576/023* (2013.01)

(58) Field of Classification Search
CPC ... A61B 5/0432; A61B 5/04325; A61B 5/044; A61B 5/0452; A61B 5/04525; A61B 5/0456; A61B 5/046; A61B 5/7235; A61B 5/7246; A61B 5/7275; A61B 5/7282; A61B 5/742
See application file for complete search history.

(56) References Cited

U.S. PATENT DOCUMENTS

| 9,392,948 | B2* | 7/2016 | Briggs | ............... | A61B 5/04012 |
| | | | | | 600/509 |
| 2004/0059237 | A1 | 3/2004 | Narayan et al. | | |
| 2012/0108994 | A1 | 5/2012 | Patel et al. | | |

OTHER PUBLICATIONS

A. Buttu, A. Forclaz, P. Pascale, S. M. Narayan, E. Pruvot and J. M. Vesin, "Morphological study of intracardiac signals as a new tool to track the efficiency of stepwise ablation of persistent atrial fibrillation," 2011 Computing in Cardiology, Hangzhou, 2011, pp. 169-172.*

Ciaccio, Edward J. et al. "Differences in Repeating Patterns of Complex Fractionated Left Atrial Electrograms in Longstanding Persistent Atrial Fibrillation as Compared With Paroxysmal Atrial Fibrillation." Circulation. Arrhythmia and electrophysiology 4.4 (2011): 470-477. PMC. Web. Oct. 15, 2017.*

Ravelli et al. "Anatomic Localization of Rapid Repetitive Sources in Persistent Atrial Fibrillation: Fusion of Biatrial CT Images With Wave Similarity/Cycle Length Maps". JACC: Cardiovascular Imaging, vol. 5, Issue 12, Dec. 2012, pp. 1211-1220.*

L. Faes, G. Nollo, R. Antolini, F. Gaita and F. Ravelli, "A method for quantifying atrial fibrillation organization based on wave-morphology similarity," in IEEE Transactions on Biomedical Engineering, vol. 49, No. 12, pp. 1504-1513, Dec. 2002.*

Ng, Jason et al. "Electrogram Morphology Recurrence Patterns during Atrial Fibrillation." Heart rhythm : the official journal of the Heart Rhythm Society11.11 (2014): 2027-2034. PMC. Web. Oct. 15, 2017.*

Supplemental Material to Lin et al. "Prevalence, Characteristics, Mapping, and Catheter Ablation of Potential Rotors in Nonparoxysmal Atrial Fibrillation". Circulation: Arrhythmia and Electrophysiology. 2013;6:851-858, originally published Oct. 15, 2013.*

International Search Report and Written Opinion dated Feb. 13, 2015 for International Application No. PCT/US2014/063819, 11 pages.

Eckmann et al., "Recurrence plots of dynamical systems," Eurphys. Left. (1987) 4:973-977.

Morillo et al., "Chronic rapid atrial pacing—Structural, functional, and electrophysiological characteristics of a new model of sustained atrial fibrillation," Circulation 91:1588-1595 (1995).

Botteron et al, "A technique for measurement of the extent of spatial organization of atrial activation during atrial fibrillation in the intact human heart," IEEE Trans Biomed Eng 42(6):579-586, 1995.

Eckmann et al., "Recurrence Plots of Dynamical Systems," Europhys. Left. 4(9):973-977, 1987.

Morillo et al., "Chronic Rapid Atrial Pacing," Circulation 91:1588-1595, 1995.

Ng et al., "Iterative method to detect atrial activations and measure cycle length from electrograms during atrial fibrillation," IEEE Trans Biomed Eng. 61:273-278, 2014.

Orton, "Thoracic wall," In: Textbook of Small Animal Surgery, edited by Slatter D. Philadelphia, PA, USA: Saunders, pp. 374-375, 2003.

U.S. Appl. No. 61/819,455, filed May 3, 2013.

Communication for EP App. No. 14858037.6, dated Jun. 6, 2017, and extended European Search report, dated May 29, 2017, 10 pages.

Krummen, D., et al. "Centrifugal Gradients of Rate and Organization in Human Atrial Fibrillation", PACE—Pacing and Clincal Electrophysiology., vol. 32, No. 11, Nov. 1, 2009 (Nov. 1, 2009), pp. 1366-1378, XP055376345, US ISSN: 0147-8389, DOI: 10.1111j., 1540-8159.2009.02525.x.

Lin, Y.-J, et al., "Prevalence Characteristics, Mapping, and Catheter Ablation of Potential Rotors in Nonparoxysmal Atrial Fibrillation", Circulation. Arrhythmia and Electrophysiology, vol. 6, No. 5, Aug. 27, 2013, pp. 351-858, XP055376351, United States, ISSN: 1941-3149, DOI: 10.1161/CIRCEP.113.000318.

* cited by examiner

| ATRIUM | SITE | CL | | REC% | | $CL_R$ | |
|---|---|---|---|---|---|---|---|
| | | MEAN±SD (MS) | # OF MIN | MEAN±SD (%) | # OF MAX | MEAN±SD (MS) | # OF MIN |
| RIGHT ATRIUM | APPENDAGE | 150±20 | 2 | 40±17 | 0 | 467±236 | 1 |
| | LATERAL WALL | 154±35 | 4 | 43±24 | 1 | 1874±6362 | 1 |
| | SVC/RA JUNCTION | 171±39 | 1 | 52±26 | 2 | 493±425 | 0 |
| | POSTERIOR WALL | 155±28 | 1 | 35±15 | 0 | 572±293 | 0 |
| | IVC/RA JUNCTION | 166±36 | 1 | 39±15 | 1 | 551±440 | 0 |
| | SEPTUM | 162±29 | 1 | 34±19 | 1 | 669±477 | 1 |
| LEFT ATRIUM | SEPTUM | 156±25 | 0 | 36±20 | 2 | 676±613 | 1 |
| | RSPV | 159±16 | 0 | 45±27 | 0 | 845±1462 | 0 |
| | RIPV | 156±19 | 1 | 40±23 | 2 | 614±536 | 2 |
| | ROOF | 153±18 | 5 | 46±25 | 1 | 636±1010 | 2 |
| | POSTERIOR WALL | 155±24 | 1 | 38±20 | 1 | 570±365 | 1 |
| | LSPV | 156±19 | 0 | 57±29 | 4 | 420±331 | 3 |
| | LIPV | 157±13 | 2 | 50±26 | 3 | 492±543 | 5 |
| | APPENDAGE | 154±21 | 0 | 58±23 | 1 | 322±137 | 2 |

*FIG. 10*

SHORTEST CL IN EACH REGION (IN MS, OVERALL SHORTEST BOLD AND ITALICIZED)

| DOG | PLA1 | PLA2 | LAA | RAFW | RAA |
|---|---|---|---|---|---|
| 1 | 87 | *83* | 89 | 88 | 102 |
| 2 | 94 | *93* | 114 | 101 | 108 |
| 3 | 96 | 98 | 89 | 98 | *76* |
| 4 | *82* | 85 | *82* | 91 | 88 |
| 5 | 97 | 99 | 103 | *92* | 114 |
| 6 | 63 | *58* | 63 | 78 | 80 |

*FIG. 14A*

HIGHEST REC% IN EACH REGION (IN %, OVERALL HIGHEST BOLD AND ITALICIZED)

| DOG | PLA1 | PLA2 | LAA | RAFW | RAA |
|---|---|---|---|---|---|
| 1 | 86 | *100* | 86 | 89 | 84 |
| 2 | 94 | *100* | 84 | 98 | 97 |
| 3 | 91 | *100* | 95 | 99 | 95 |
| 4 | 98 | 99 | 86 | 92 | *99* |
| 5 | 88 | 87 | 97 | 89 | *100* |
| 6 | 75 | 87 | 95 | 92 | *93* |

*FIG. 14B*

SHORTEST $CL_R$ (IN MS, OVERALL SHORTEST BOLD AND ITALICIZED)

| DOG | PLA1 | PLA2 | LAA | RAFW | RAA |
|---|---|---|---|---|---|
| 1 | 108 | *88* | 110 | 102 | 151 |
| 2 | 119 | *111* | 151 | 160 | 147 |
| 3 | 112 | 111 | 99 | 124 | *80* |
| 4 | 93 | 99 | *86* | 107 | 90 |
| 5 | 118 | 122 | *111* | 132 | 152 |
| 6 | 89 | 70 | *69* | 106 | 91 |

*FIG. 14C*

SYSTEM AND METHOD FOR DETERMINING ELECTROGRAM MORPHOLOGY RECURRENCE PATTERNS AND RATES DURING ATRIAL FIBRILLATION

CROSS-REFERENCE TO RELATED APPLICATIONS

This application is a National Stage Entry, submitted under 35 U.S.C. 371, of International Application No. PCT/US14/63819, filed Nov. 4, 2014, which claims the benefit of U.S. Provisional Application No. 61/899,453, filed Nov. 4, 2013, the content of each herein incorporated by reference in their entirety.

FIELD OF THE DISCLOSURE

This disclosure relates to a system and method for identifying at least one location of interest for perpetuation or persistence of arrhythmia or atrial fibrillation

BACKGROUND

Atrial fibrillation is a complex and seemingly chaotic arrhythmia that has been described as an emerging epidemic. The empirically validated approaches of electrically isolating the pulmonary veins (and antrum) from the left atrium with ablation have demonstrated only moderate success rates, with paroxysmal atrial fibrillation patients responding better than those with persistent atrial fibrillation. Success rates of these procedures can be improved by adding additional ablation or surgical lesions in the atria. Strategies moving beyond the current empirical approaches are needed to improve treatment. Although intracardiac electrical recordings from catheters are routinely obtained during ablation procedures, use of these recordings by clinicians to guide ablation has been limited due to the lack of understanding of the complex nature of these electrograms, specifically how to use these electrograms to identify sites that are critical for the maintenance and perpetuation of these arrhythmias.

SUMMARY

In one embodiment, a method of identifying at least one location of interest for perpetuation or persistence of arrhythmia or atrial fibrillation is disclosed. A repeatability of electrogram morphologies is determined from electrical recordings within at least one atrium.

In another embodiment, a method of identifying at least one location of interest for perpetuation or persistence of arrhythmia or atrial fibrillation is disclosed. Cycle lengths of repeating electrogram morphologies are determined at a plurality of locations within at least one atrium.

In still another embodiment, a system for determining at least one location of interest for perpetuation or persistence of arrhythmia or atrial fibrillation is disclosed. The system includes at least one electrogram device, at least one processor, and a memory. The at least one electrogram device is configured to record electrograms at a plurality of locations within at least one atrium. The at least one processor is in electronic communication with the at least one electrogram device. The memory is in electronic communication with the at least one processor. The memory includes programming code for execution by the at least one processor. The programming code is configured to determine repeatability of electrogram morphologies at each of the plurality of locations within the at least one atrium.

In an additional embodiment, a system for identifying at least one location of interest for perpetuation or persistence of arrhythmia or atrial fibrillation is disclosed. The system includes at least one electrogram device, at least one processor, and a memory. The at least one electrogram device is configured to record electrograms at a plurality of locations within at least one atrium. The at least one processor is in electronic communication with the at least one electrogram device. The memory is in electronic communication with the at least one processor. The memory includes programming code for execution by the at least one processor. The programming code is configured to determine cycle lengths of repeating electrogram morphologies at the plurality of locations within the at least one atrium.

The scope of the present disclosure is defined solely by the appended claims and is not affected by the statements within this summary.

BRIEF DESCRIPTION OF THE DRAWINGS

The disclosure can be better understood with reference to the following drawings and description. The components in the figures are not necessarily to scale, emphasis instead being placed upon illustrating the principles of the disclosure.

FIG. 10 illustrates a table which shows the mean and standard deviations of CL, recurrence percentage, and $CL_R$ for 14 atrial sites as well as the distribution of the minimum CL and $CL_R$ sites and maximum recurrence percentage sites from 19 patients;

FIG. 14 illustrates table which show the results for six dogs at each of five atrial sites;

DETAILED DESCRIPTION

The disclosure relates to morphology recurrence analysis which is a signal processing technique that characterizes the changing patterns of electrogram morphologies during arrhythmia or atrial fibrillation. This morphology recurrence analysis may be used to locate locations of interest in at least one atrium which may be causing or casually related to the arrhythmia or atrial fibrillation. A surgical or interventional procedure, such as ablation or other techniques known to those of ordinary skill in the art, may then be carried out on these identified locations of interest to reduce or eliminate the arrhythmia or atrial fibrillation.

Figure 1:
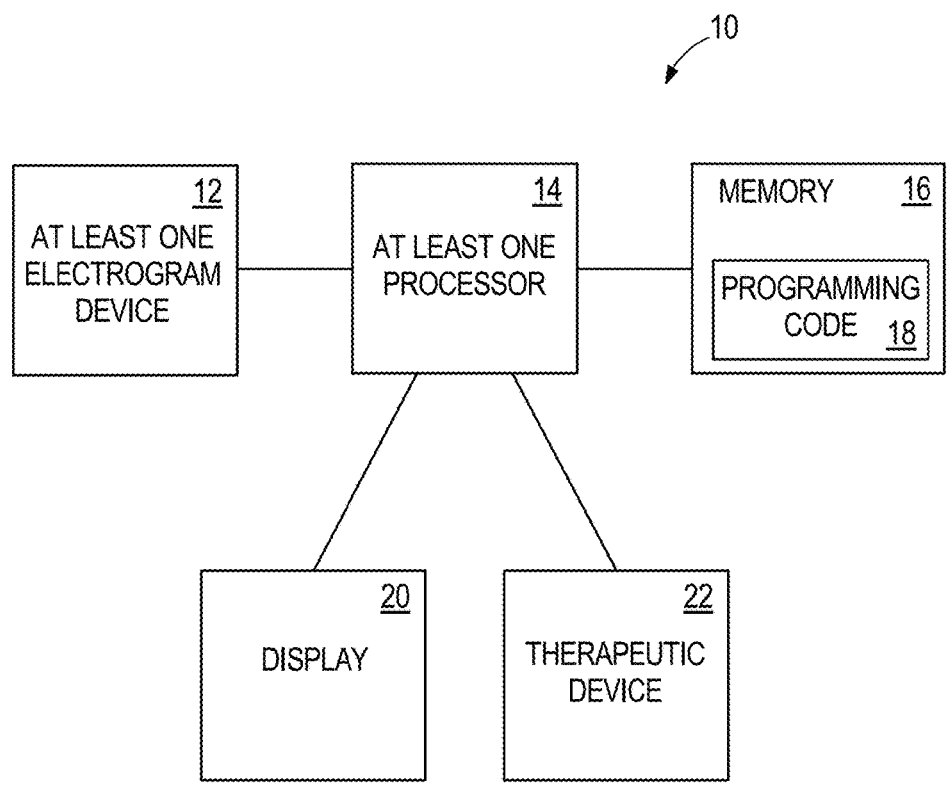
FIG. 1 illustrates a box diagram of one embodiment of a system which may be used to determine at least one location of interest for perpetuation or persistence of arrhythmia or atrial fibrillation.

FIG. 1 illustrates a box diagram of one embodiment of a system 10 which may be used to determine at least one location of interest for perpetuation or persistence of arrhythmia or atrial fibrillation. The system 10 includes at least one electrogram recording device 12, at least one processor 14, a memory 16, programming code 18, a display 20, and a surgical, treatment, or therapeutic device 22. The at least one processor 14 is in electronic communication with the at least one electrogram device 12. The memory 16 is in electronic communication with the at least one processor 14. The memory contains the programming code 18 for execution by the at least one processor 14. The display 20 is in electronic communication with the at least one processor 14. The surgical, treatment, or therapeutic device 22 is in electronic communication with the at least one processor 14.

The at least one electrogram device 12 comprises a device which is configured to record electrograms at a plurality of locations within at least one atrium. In one embodiment, the at least one electrogram device 12 may comprise an electrode catheter. In other embodiments, the at least one electrogram device 12 may comprise any type of device known to those of ordinary skill in the art for recording electrograms at a plurality of locations within at least one atrium. In one embodiment, the at least one electrogram device 12 may be moved from location to location within the at least one atrium to record the electrograms at the plurality of locations. In another embodiment, the at least one electrogram device 12 may simultaneously record electrograms at the plurality of locations within the at least one atrium.

The programming code 18 is configured to determine repeatability of electrogram morphologies at each of the plurality of locations within the at least one atrium. In one embodiment, the programming code 18 may utilize one or more cross-correlation algorithms to determine the repeatability of the electrogram morphologies. In another embodiment, the programming code 18 may utilize any type of algorithm known to those of ordinary skill in the art to determine the repeatability of the electrogram morphologies.

The programming code 18 is configured to identify individual activations at each of the plurality of locations within the at least one atrium, and to determine the repeatability of the electrogram morphologies at each of the plurality of locations within the at least one atrium using the identified individual activations. The electrogram repeatability determination may be done using any method disclosed herein in the instant disclosure or using any method known to those of ordinary skill in the art. The programming code 18 is configured to generate an illustration on the display 20 showing the repeatability of the electrogram morphologies at each of the plurality of locations within the at least one atrium. The illustration may comprise a plot, a graph, a representation, a table, a chart, or another type of illustration.

The programming code 18 is configured to identify the at least one location of interest for perpetuation or persistence of the arrhythmia or the atrial fibrillation as being that which has electrogram morphologies of high repeatability based on preset parameters. The preset parameters may comprise the exceeding of a high repeatability threshold, the identification of the location having the absolute maximum repeatability, the location having a repeatability being in the top preset number of repeatability values of the plurality of locations (i.e. such as the location having a repeatability falling within the top 5 repeatability values of the plurality of locations), or other preset parameters. The high electrogram repeatability determination may be done using any method disclosed herein within the instant disclosure or using any method known to those of ordinary skill in the art.

In another embodiment, the programming code 18 may be configured to determine cycle lengths of the repeating electrogram morphologies at the plurality of locations within the at least one atrium. In one embodiment, the method and system disclosed in U.S. Patent Application Ser. No. 61/819,455, which is hereby incorporated by reference, may be used to determine the cycle lengths of the electrogram morphologies, and then the methodology disclosed in the instant disclosure may be used to determine the cycle lengths of the repeating electrogram morphologies at the plurality of locations with the at least one atrium. In another embodiment, any method and system known to those of ordinary skill in the art may be used to determine the cycle lengths of the repeating electrogram morphologies. The programming code 18 may be configured to generate an illustration on the display 20 showing the repeatability of the electrogram morphologies at each of the plurality of locations within the at least one atrium, and to additionally show cycle lengths of high repeating electrogram morphologies at the plurality of locations. The illustration may comprise a plot, a graph, a representation, a table, a chart, or another type of illustration. The programming code 18 may be configured to identify the at least one location of interest for perpetuation or persistence of the arrhythmia or the atrial fibrillation as being that which has high electrogram repeatability and a short cycle length based on preset parameters.

The preset parameters may comprise the exceeding of a high repeatability threshold, the identification of the location having the absolute maximum repeatability, the location having a repeatability being in the top preset number of repeatability values of the plurality of locations (i.e. such as the location having a repeatability falling within the top 5 repeatability values of the plurality of locations), or other preset parameters. The preset parameters for the short cycle length may comprise being lower than a short cycle length threshold, the identification of the high repeatability location having the absolute lowest cycle length, the location having a cycle length being in the shortest preset number of cycle length values of the plurality of locations (i.e. such as the location having a cycle length falling within the shortest 3 cycle length values of the plurality of locations), or other preset parameters.

In both embodiments, the programming code 18 is configured to direct the surgical, treatment, or therapeutic device 22 to the identified at least one location of interest within the at least one atrium to reduce or eliminate the arrhythmia or the atrial fibrillation. The surgical, treatment, or therapeutic device 22 may comprise any type of device known to those of ordinary skill in the art for reducing or eliminating arrhythmia or atrial fibrillation such as ablation devices, devices for releasing a chemical, or other types of devices. In other embodiments, one or more of the components of the system 10 may be removed or modified, or one or more additional components may be added. Moreover, the system 10 may utilize any of the embodiments, methods, or algorithms disclosed in the instant disclosure as well as using any components, methods, or algorithms known to those of ordinary skill in the art.

Figure 2:
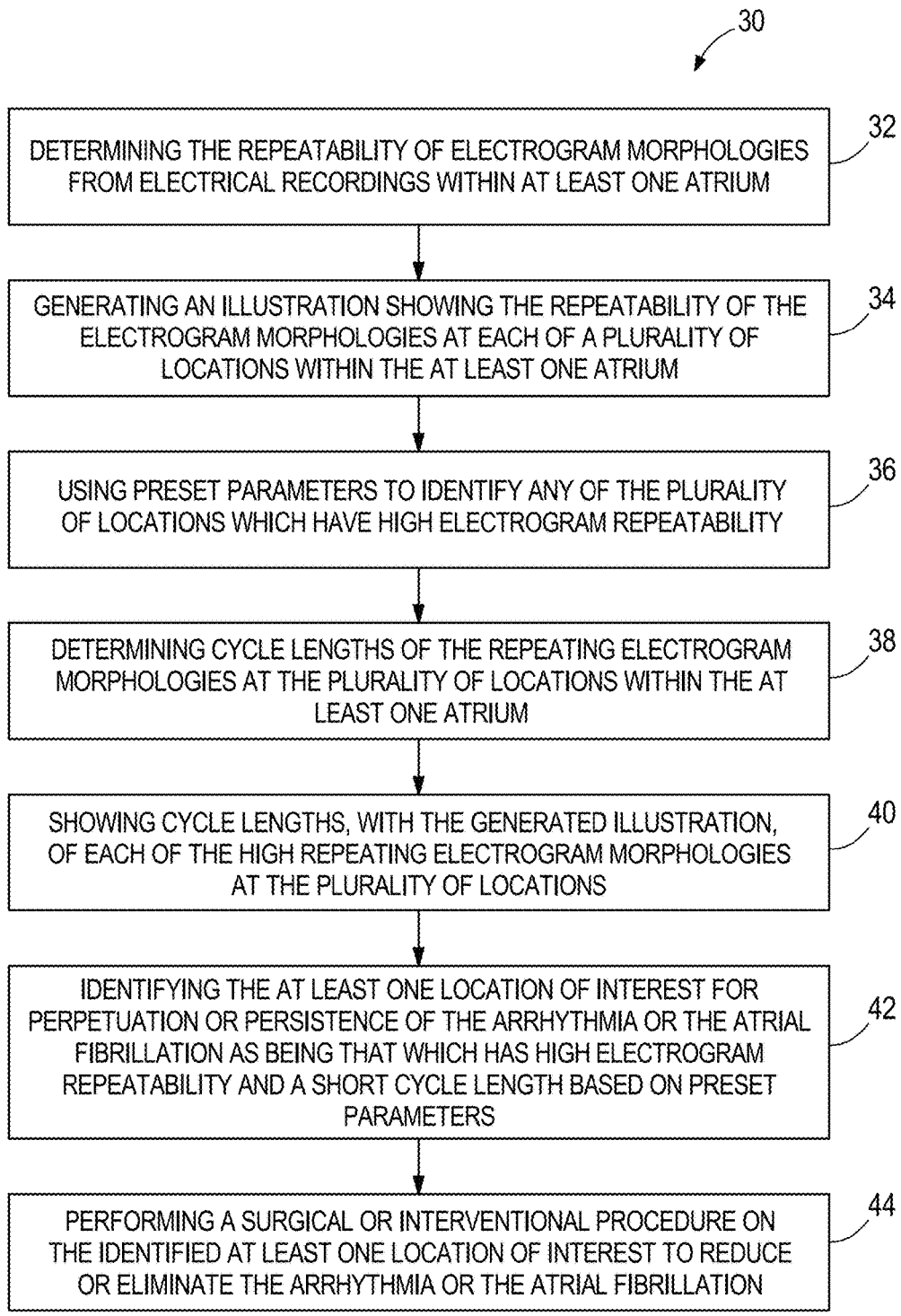
FIG. 2 is a flowchart illustrating one embodiment of a method of identifying at least one location of interest for perpetuation or persistence of arrhythmia or atrial fibrillation.

FIG. 2 is a flowchart illustrating one embodiment of a method 30 of identifying at least one location of interest for perpetuation or persistence of arrhythmia or atrial fibrillation. The method 30 may utilize the system 10 of FIG. 1. In step 32, the repeatability of electrogram morphologies may be determined from electrical recordings within at least one atrium. In one embodiment, step 32 may utilize one or more cross-correlation processes as disclosed in the instant disclosure to determine the repeatability of the electrogram morphologies. In another embodiment, step 32 may utilize any type of process or algorithm known to those of ordinary skill in the art to determine the repeatability of the electrogram morphologies. In one embodiment, step 32 may comprise: recording electrograms at a plurality of locations within the at least one atrium; identifying individual activations at each of the plurality of locations; and determining the repeatability of the electrogram morphologies at each of the plurality of locations within the at least one atrium using the identified individual activations. In step 34, an illustration may be generated showing the repeatability of the electrogram morphologies at each of a plurality of locations within the at least one atrium. The illustration may comprise a plot, a graph, a representation, a table, a chart, or another type of illustration.

In step 36, preset parameters may be used to identify any of the plurality of locations which have high electrogram repeatability. The preset parameters may comprise the exceeding of a high repeatability threshold, the identification of the location having the absolute maximum repeatability, the location having a repeatability being in the top preset number of repeatability values of the plurality of locations (i.e. such as the location having a repeatability falling within the top 5 repeatability values of the plurality of locations), or other preset parameters. In one embodiment, the locations identified as having high repeatability may be identified as being the at least one location of interest for perpetuation or persistence of the arrhythmia or the atrial fibrillation.

In step 38, cycle lengths of the repeating electrogram morphologies are determined at the plurality of locations within the at least one atrium. In one embodiment, the method and system disclosed in U.S. Patent Application Ser. No. 61/819,455, which is hereby incorporated by reference, may be used to determine the cycle lengths of the individual electrograms, and then the methodology disclosed in the instant disclosure may be used to determine the cycle lengths of the repeating electrogram morphologies at the plurality of locations with the at least one atrium. In another embodiment, any method and system known to those of ordinary skill in the art may be used to determine the cycle lengths of the repeating electrogram morphologies. In step 40, the generated illustration may also show cycle lengths of each of the high repeating electrogram morphologies at the plurality of locations. In step 42, the at least one location of interest for perpetuation or persistence of the arrhythmia or the atrial fibrillation may be identified as being that which has high electrogram repeatability and a short cycle length based on preset parameters.

The preset parameters for the high electrogram repeatability may comprise the exceeding of a high repeatability threshold, the identification of the location having the absolute maximum repeatability, the location having a repeatability being in the top preset number of repeatability values of the plurality of locations (i.e. such as the location having a repeatability falling within the top 5 repeatability values of the plurality of locations), or other preset parameters. The preset parameters for the short cycle length may comprise being lower than a short cycle length threshold, the identification of the high repeatability location having the absolute lowest cycle length, the location having a cycle length being in the shortest preset number of cycle length values of the plurality of locations (i.e. such as the location having a cycle length falling within the shortest 3 cycle length values of the plurality of locations), or other preset parameters.

In step 44, a surgical or interventional procedure may be performed on the identified at least one location of interest to reduce or eliminate the arrhythmia or the atrial fibrillation. The surgical or interventional procedure may comprise ablation or any other type of surgical or interventional procedure known to those of ordinary skill in the art for reducing or eliminating arrhythmia or atrial fibrillation. In other embodiments, any of the steps of the method 30 may not be followed, may be modified in substance or in order, or one or more additional steps may be added. Moreover, the method 30 may utilize any of the embodiments, systems, methods, or algorithms disclosed in the instant disclosure as well as using any systems, methods, or algorithms known to those of ordinary skill in the art.

Figure 3:
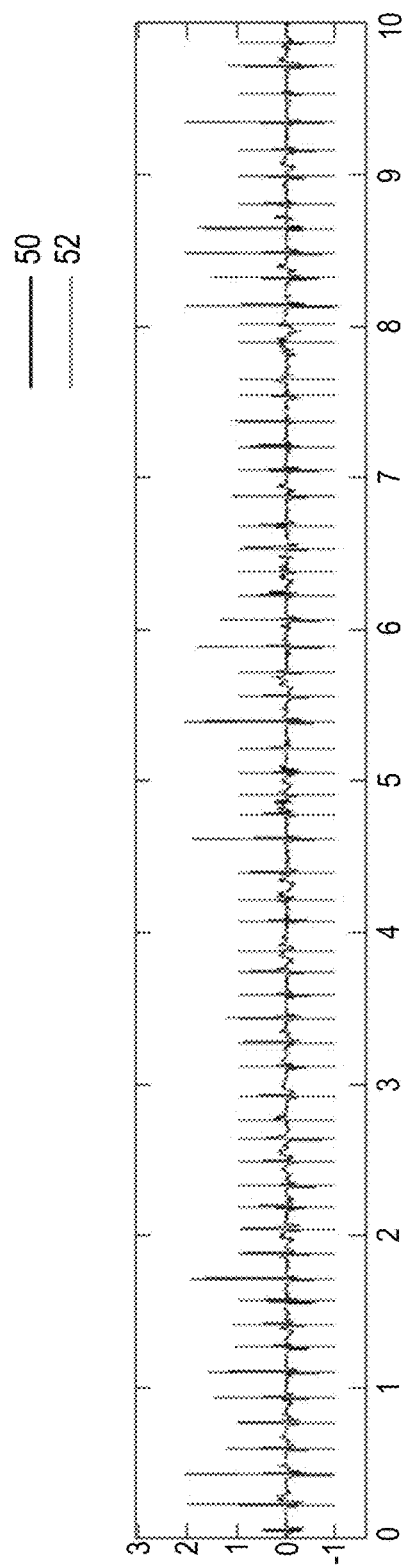
FIG. 3 illustrates one embodiment of a graph showing a representative atrial fibrillation electrogram signal and detected activations which were measured for one patient at one location of the patient's atrium.

FIG. 3 illustrates one embodiment of a graph showing a representative atrial fibrillation electrogram signal 50 and detected activations 52 which were measured for one patient at one location of the patient's atrium. The signal 50 and activations 52 were detected using the system 10 of FIG. 1 and the method 30 of FIG. 2. For each activation 52, a 100 millisecond segment was centered at the time the maximum slope was extracted. In one embodiment, the method and system disclosed in U.S. Patent Application Ser. No. 61/819,455, which is hereby incorporated by reference, may be used to determine the activations 52. In another embodiment, any method and system known to those of ordinary skill in the art may be used to determine the activations 52.

Figure 4:
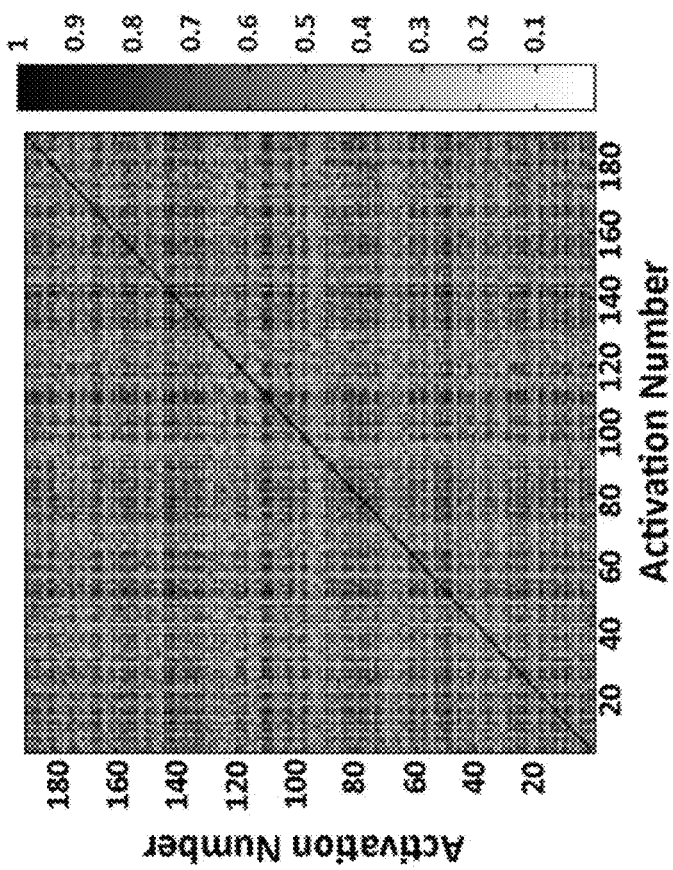
FIG. 4 illustrates one embodiment of a table cross-correlating each of the activations detected from electrograms for one patient at one location of the patient's atrium to obtain cross-correlation values of each electrogram to all the other electrograms. This information is used to define the recurrence index indicating the recurrence of the most common electrogram morphologies.

FIG. 4 illustrates one embodiment of a table cross-correlating each of the activations detected from electrograms for one patient at one location of the patient's atrium to obtain cross-correlation values from which the recurrence (i.e. repeatability) of the electrogram morphologies can be assessed. Recurrence index is defined as being the number of the most common electrogram morphology as the percentage of the total number of activations. Cross-correlation is known to those of ordinary skill in the art. In the instant embodiment, a 100 millisecond (ms) window for each detected activation in the electrogram recording with 40 Hz high pass filtering was cross-correlated with every other detected activation in the electrogram recording at the particular location in the patient's atrium. In other embodiments, varying duration windows and varying frequency filtering may be used. The table was obtained using the system 10 of FIG. 1 and the method 30 of FIG. 2. The maximum normalized cross-correlation values were determined for each combination of activations. The result was a set of N times N maximum cross-correlation values, where N is the number of activations (in this example N=6). In the table, the x-axis and the y-axis represent the first and second activation templates, respectively, that are cross-correlated.

Cross-correlation values closer to 1 indicates greater similarity (i.e. higher repeatability) in electrogram morphology between two activations. Cross-correlation values closer to 0 indicate less similarity (i.e. lower repeatability) in electrogram morphology between two activations. The line of identity where the x-value equals the y-value always has cross-correlation values of 1, as each activation is compared with itself. As an example, the 0.94 cross-correlation value indicates two activations (first and third in this example) which are highly similar. In one embodiment, any cross-correlation value above 0.80 between two activations is deemed to have a high repeatability. These cross-correlation values for all combinations of activations can then be used to identify the activation that represents the most common morphology. A recurrence index or recurrence percentage can then be calculated by determining the percentage of activations that are highly correlated with this most common morphology. In other embodiments, preset parameters may be used to determine what cross-correlation values comprise a high electrogram repeatability such as the use of a high repeatability threshold (i.e. a cross-correlation values over the high cross-correlation threshold would be held to have a high repeatability), the identification of the highest recurrence index value as having a high repeatability, the identification of the recurrence indexes having values in the top preset number of recurrence index values (i.e. such as the recurrence index value falling within the top 5 recurrence index values), or other preset parameters. In still other embodiments, any type of system, repeatability method, illustration, or illustration method may be used to determine and indicate the repeatability of the electrogram morphology.

Figure 5:
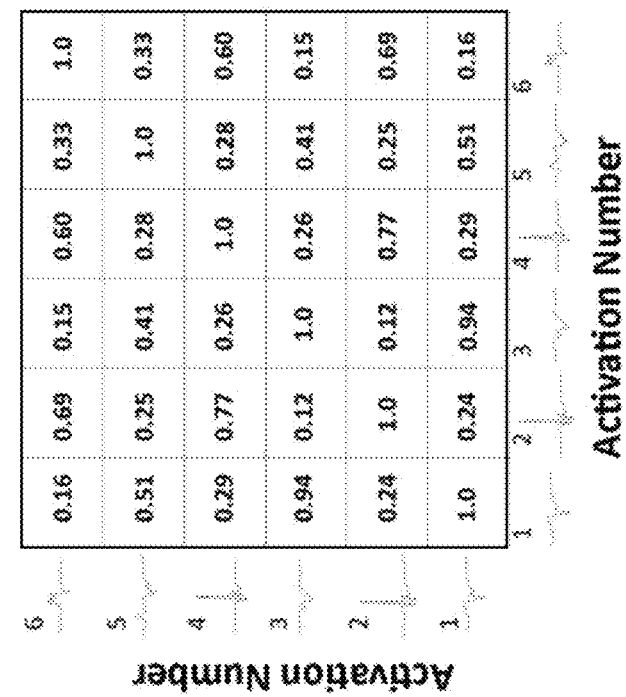
FIG. 5 illustrates one embodiment of a morphology recurrence plot which was prepared using data of a cross-correlation table similar to that of FIG. 4 but based on over 180 detected cross-correlated activations.

FIG. 5 illustrates one embodiment of a morphology recurrence plot which was prepared using data of a cross-correlation table similar to that of FIG. 4 but based on over 180 detected cross-correlated activations. The morphology recurrence plot may be color-coded so that the reader can determine the areas of the electrogram morphology having the highest recurrence (i.e. highest repeatability) based on the cross-correlation values being closer to 1.0 and so that the reader can also determine the pattern of recurrence. The checker-board pattern of FIG. 5 suggests there is a dominant morphology that periodically recurs for the duration of the electrogram recording. In still other embodiments, any type of system, repeatability method, illustration, or illustration method may be used to determine and indicate the repeatability of the electrogram morphology.

Figure 6:
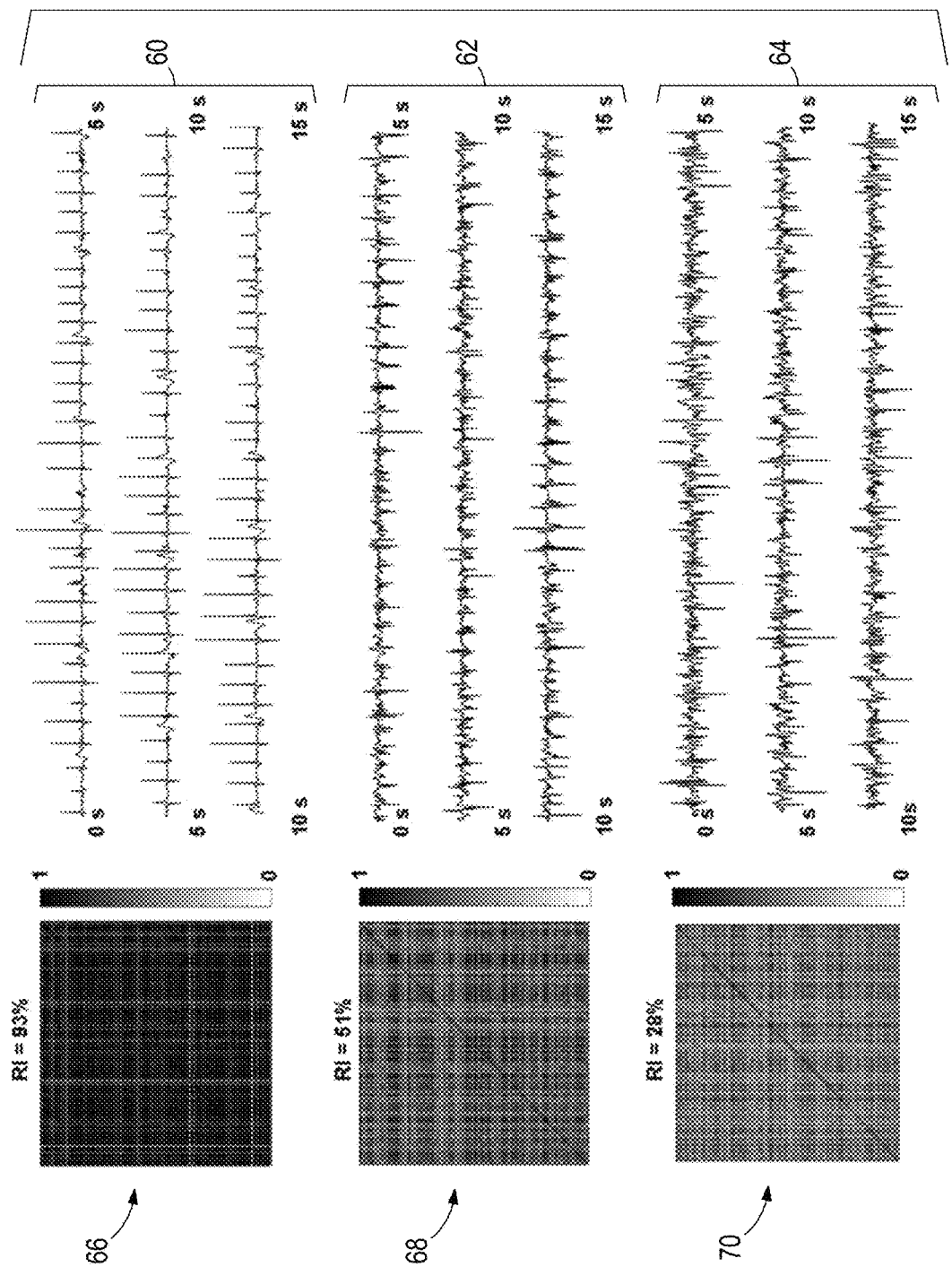
FIG. 6 illustrates one embodiment of varying electrogram morphologies and their corresponding morphology recurrence plots.

FIG. 6 illustrates one embodiment of varying electrogram morphologies 60, 62, and 64 and their corresponding morphology recurrence plots 66, 68, and 70. FIG. 6 was obtained using the system 10 of FIG. 1 and the method 30 of FIG. 2. As shown, electrogram morphology 60 has the highest recurrence percentage of 93%, electrogram morphology 62 has the next highest recurrence percentage of 51%, and electrogram morphology 64 has the lowest recurrence percentage of 28%. In still other embodiments, any type of system, repeatability method, illustration, or illustration method may be used to determine and indicate the repeatability of the electrogram morphology.

Figure 7:
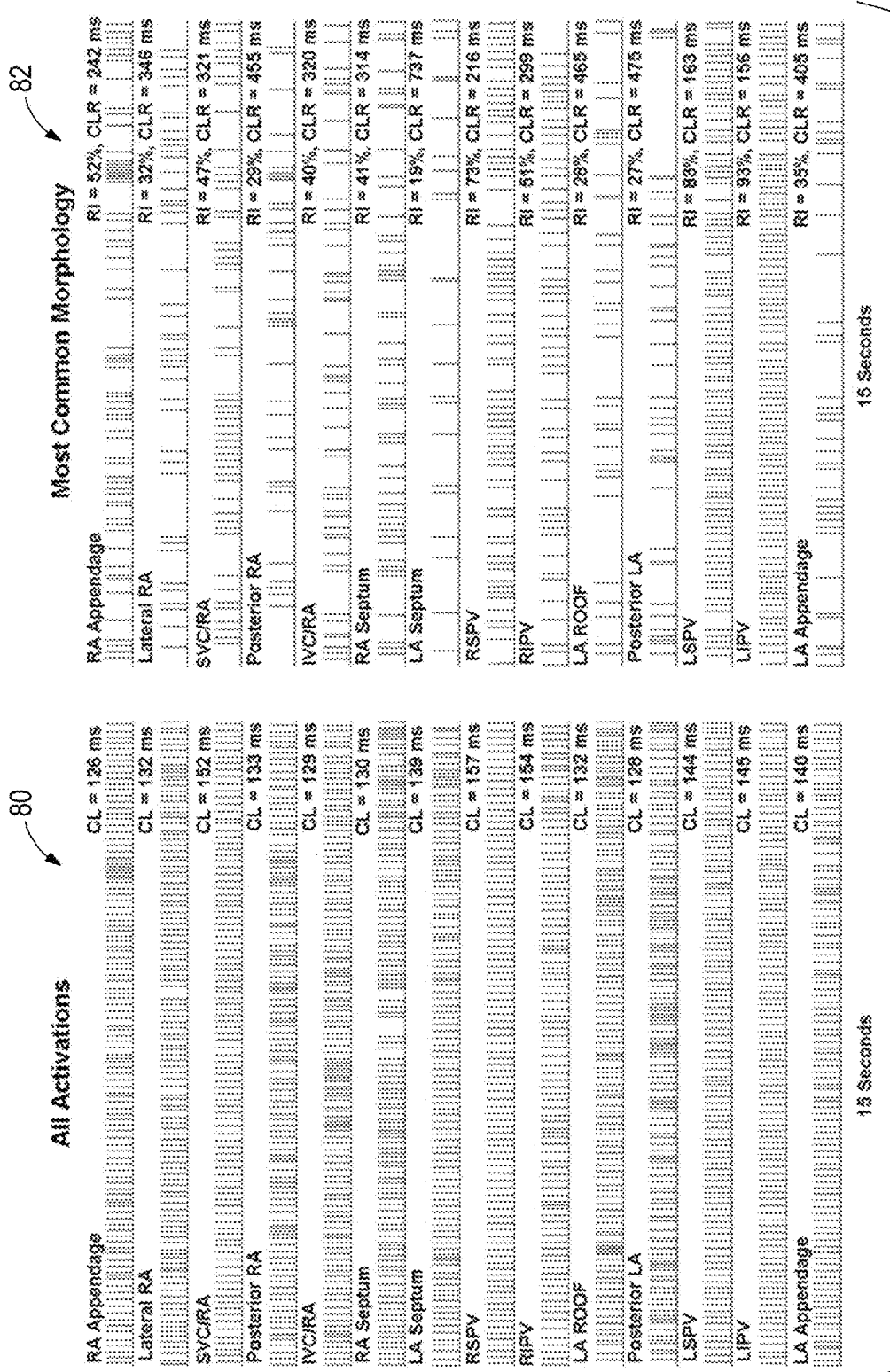
FIG. 7 illustrates one embodiment showing on the left pictorial representations of all activations detected at different atrial locations for a patient identifying the cycle length of the activations at each location, and showing on the right pictorial representations of the most common repeating electrogram morphology detected at each atrial location for the patient identifying the recurrence index and the cycle length for the most common repeating electrogram morphologies.

FIG. 7 illustrates one embodiment showing on the left pictorial representations 80 of all activations detected at different atrial locations for a patient identifying the cycle length (CL) of the activations at each location, and showing on the right pictorial representations 82 of the times of most common repeating electrogram morphology detected at each atrial location for the patient indicating the recurrence index (RI) and the cycle length ($CL_R$) for the most common repeating electrogram morphologies ($CL_R$=CL/RI). In one embodiment, the method and system disclosed in U.S. Patent Application Ser. No. 61/819,455, which is hereby incorporated by reference, may be used to determine the cycle lengths between each and every activation. In another embodiment, any method and system known to those of ordinary skill in the art may be used to determine the cycle lengths of the activations at each location and to determine the cycle lengths for the most common repeating electrogram morphologies. FIG. 7 was obtained using the system 10 of FIG. 1 and the method 30 of FIG. 2. In still other embodiments, any type of system, repeatability method, cycle length method, illustration, or illustration method may be used to determine and indicate the repeatability and cycle length of the activations and the most common electrogram morphologies.

Figure 8:
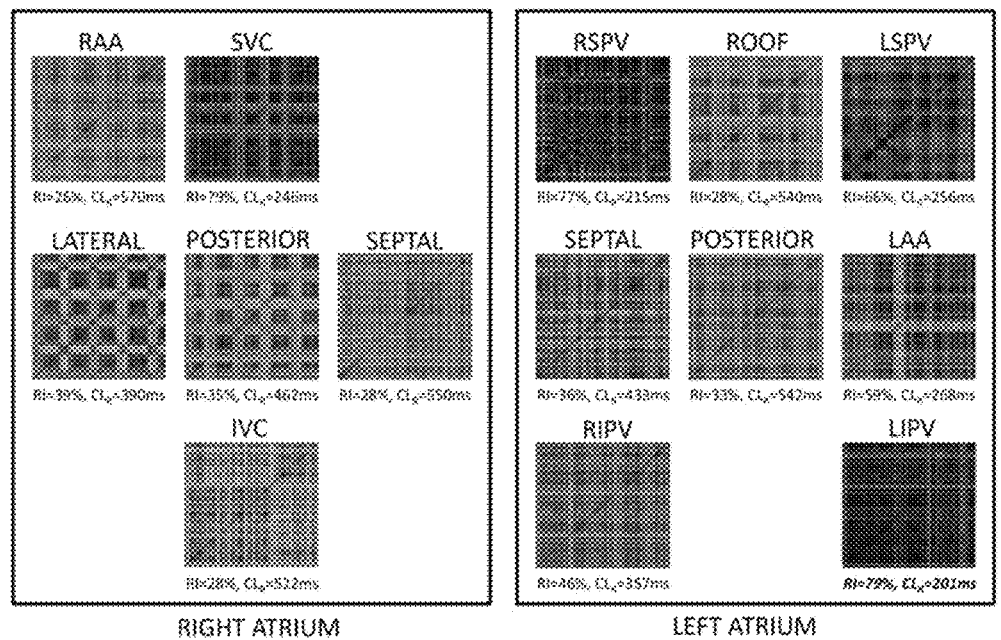
FIG. 8 illustrates one embodiment of electrogram recurrence plots which were obtained at varying atrial locations in patient A and in patient B.
Figure 8:
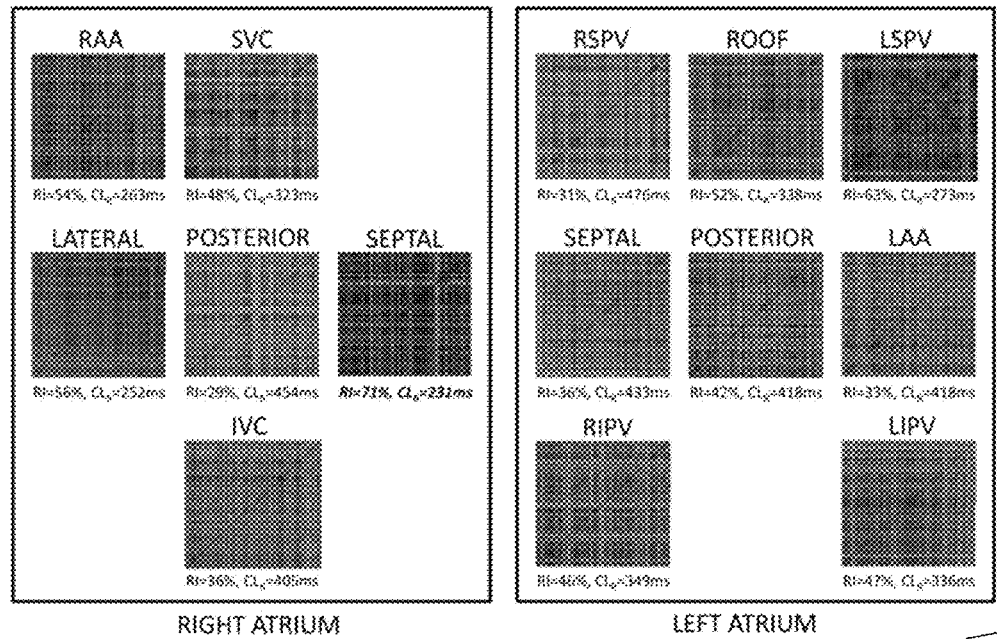

FIG. 8 illustrates one embodiment of electrogram recurrence plots which were obtained at varying atrial locations in patient A and in patient B. FIG. 8 was obtained using the system 10 of FIG. 1 and the method 30 of FIG. 2. The electrogram recurrence plots show distinct checker board patterns in the different locations indicating that the activation patterns have different levels of complexity, yet these patterns tend to have repeatable characteristics. For patient A, the highest recurrence index was 79%, which was found both near the superior vena cava (SVC) in the right atrium and near the left inferior pulmonary vein (LIPV) in the left atrium. The left atrium near the right superior pulmonary vein (RSPV) also had a high recurrence index of 77%. These locations can be easily identified in the figures with color-coding, indicating high cross-correlation for the majority of the activations. The $CL_R$ of the LIPV (201 ms), however, was much shorter than those of the RSPV (215 ms) or of the SVC (246 ms). For patient B, the highest recurring index (71%) and shortest $CL_R$ (231 ms) were found in the right atrial septum. In still other embodiments, any type of system, repeatability method, cycle length method, illustration, or illustration method may be used to determine and indicate the repeatability and cycle length of the activations and the most common electrogram morphologies.

In one study, electrograms from patients who were in AF at the time of their ablation procedure were collected prior to ablation. Patients had no prior ablation or surgical interventions in their atria. All patients provided written informed consent. The study was approved by the Institutional Review Board of Northwestern University.

Bipolar electrograms were sequentially obtained from multiple sites in the right and left atria (RA and LA) and stored on the Prucka CardioLab EP System (GE Healthcare, Waukesha, Wis.) at a sample rate of 977 Hz. The majority of the signals were collected with a Navistar catheter (Biosense Webster, Inc., Diamond Bar, C A, USA) but diagnostic catheters were used for coronary sinus recordings and were also used for multisite recordings in some patients. At least 15 seconds of electrograms were recorded at each site. Recording sites were documented using an electroanatomical mapping system (NavX, St. Jude Medical; or CartoXP, Biosense Webster). Electrograms were obtained from distributed RA (appendage, lateral wall, superior and inferior vena cava junctions, posterior wall, and septum) and LA (septum, roof, posterior wall, appendage, and the ostia of the four PVs) locations.

In addition, 36 electrograms were analyzed from seven patients with typical atrial flutter recorded from multiple sites in the RA to compare recurrence analysis during AF with a non-fibrillatory arrhythmia where stable activation patterns were expected.

MATLAB (Mathworks, Natick, Mass.) was used for all aspects of the signal processing performed in this study. Electrogram morphology recurrence plots of each AF electrogram recording were created by first performing activation detections of the electrogram signal using an iterative technique developed and validated by our laboratory. (See Ng J, Sehgal V, Ng J K, Gordon D, Goldberger J J. Iterative method to detect atrial activations and measure cycle length from electrograms during atrial fibrillation. IEEE Trans Biomed Eng. 2014; 61; 273-278, which is hereby incorporated by reference). The same algorithm was used for the detection of complex activations and in the setting of continuously fractionated sites.

Recurrence analysis was then performed on the original signal after 40 Hz high pass filtering. The morphology recurrence plot is a modification of a recurrence plot analysis first described by Eckmann et al. (See Eckmann J-P, Oliffson Kamphorst S, Ruelle D. Recurrence plots of dynamical systems. Eurphys. Lett. 1987; 4:973-977, which is hereby incorporated by reference). To create the morphology recurrence plot, a 100 ms window for each detected activation was cross-correlated with every other activation in the recording. The maximum normalized cross-correlation value was determined for each combination of activations. The result was a set of N times N maximum cross-correlation values, where N is the number of activations. The process is illustrated in a six activation example in FIG. 4. The N by N cross-correlation values can then be plotted in a two-dimensional map as shown in FIG. 5 (optionally this map can be in color). In this plot, the x-axis and y-axis represent the first and second activation template, respectively, that are cross-correlated. In one embodiment, the points representing the combination with highest cross-correlation values near 1 may be color coded in one color, while the points having the lowest cross-correlation values near 0 may be color coded in another color. The line of identity where the x-value equals the y-value always has cross-correlation values of 1, as each activation is compared with itself. The recurrence plot provides a visual means to assess how often electrogram morphologies recur and the pattern of recurrence. The "checker board" pattern of FIG. 5 suggests there is a dominant morphology that periodically recurs for the duration of the recording.

To quantify the amount of morphology recurrence, we determined the activation that best represented the most common morphology of the set of activations. This was accomplished by finding the column on the morphology recurrence plot that had the most number of cross-correlation values above 0.8, a cross-correlation value considered to be high. We defined the recurrence percentage to be the number of the most common morphology as the percentage of the total number of activations. We also calculated the mean cycle length (CL) of the most recurrent morphology ($CL_R$) by dividing the average CL for all electrograms by the recurrence percentage. We hypothesize that sites with the shortest $CL_R$ are more likely to be sites closest to a focal or reentrant driver. The $CL_R$ measure will help distinguish fast repeatable activity from slower repeatable activity that would more likely represent passive activation. We also determined the CL for each site and identified the location of the shortest CL.

Reproducibility of the recurrence percentage, $CL_R$, and CL was assessed using stable coronary sinus electrograms obtained simultaneously during the electrogram recordings of the other sites. The first and last recording during mapping of either the RA or LA was used.

Frequency domain analysis was used to determine dominant frequency (DF) and regularity index. Electrograms were classified as CFAE if their fractionation interval was less than 120 ms.

Although the study did not employ morphology recurrence analysis to guide ablation nor was it designed to assess whether morphology recurrence analysis mapping predicts ablation outcomes, preliminary data on outcomes are reported. In all patients, catheter ablation was performed only in the LA. In addition to PV ablation, roof and mitral isthmus lines were performed in four patients. Two of these patients had additional ablation at sites with CFAE. Freedom from AF was assessed after a 3 month blanking period. AF recurrence was defined as any AF or atrial tachycardia episode of 30 seconds or more documented by Holter monitor, ECG, event monitor, pacemaker, or loop recorder. Patient follow-up was available for a minimum of 6 months.

Data are presented as mean±standard deviation. Linear regression was used to compare the frequency domain measures with morphology recurrence measures. Unpaired T tests were used to compare morphology recurrence between CFAEs and non-CFAEs. Paired T test was used to compare the relative RA/LA gradients of the recurrence measures. Cox regression was used to compare freedom from AF for patients categorized by site (RA or LA) for highest recurrence percentage, shortest $CL_R$, and shortest CL. Reproducibility of two separate coronary sinus recordings were assessed using the intraclass correlation coefficient. A p-value <0.05 was considered statistically significant.

Electrograms were collected from nineteen patients (17 male, 56±11 years old). Of the 19 patients, 15 had a history of persistent AF and 4 had paroxysmal AF. Hypertension was noted in 5 patients, left ventricular systolic dysfunction (ejection fraction <50%) in 6 patients, and coronary artery disease in 2 patients.

Figure 9:
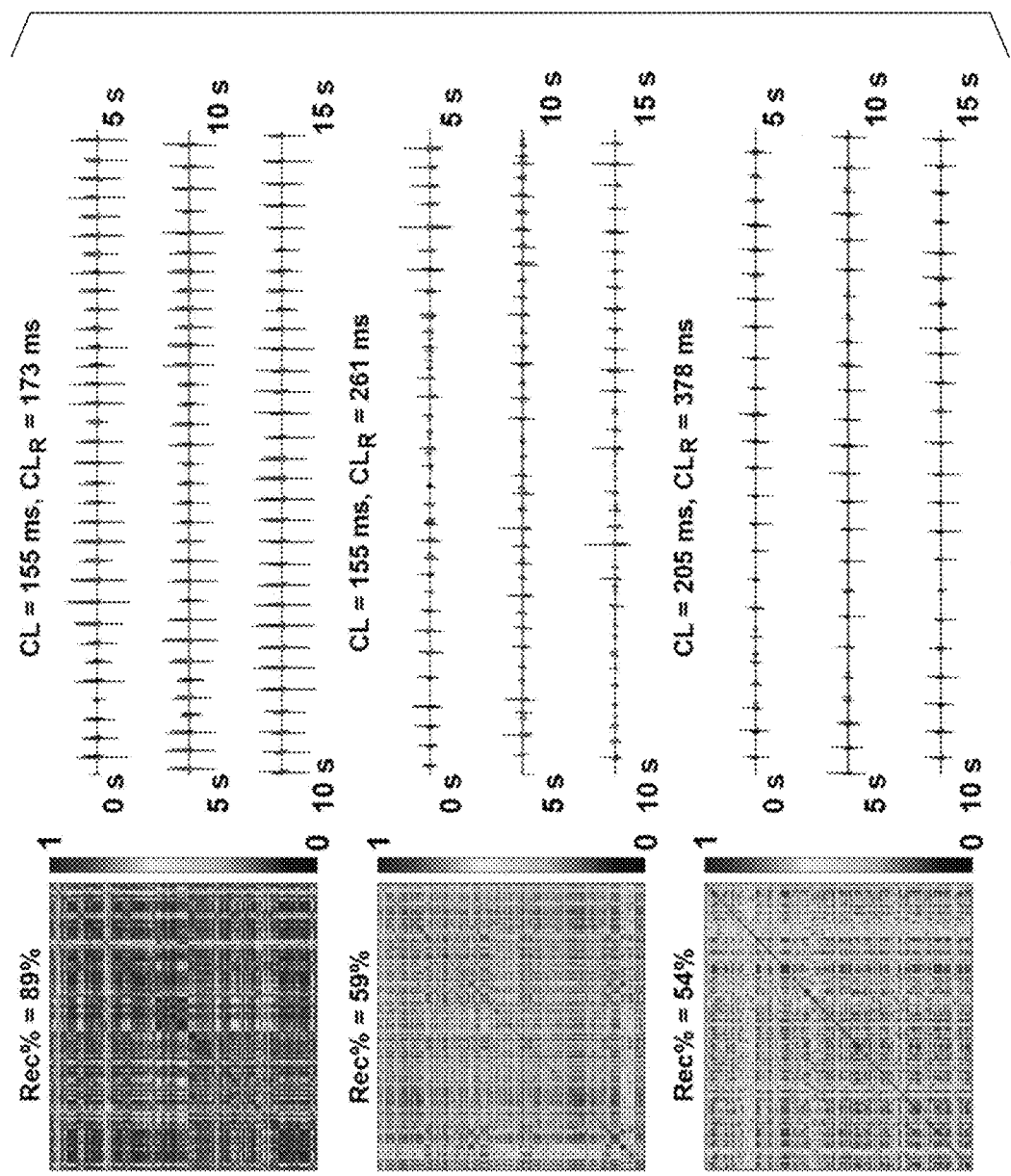
FIG. 9 illustrates examples of morphology recurrence plots and electrograms with different recurrence percentages and $CL_R$s.

FIG. 8 shows examples of morphology recurrence plots of electrograms recorded from multiple RA and LA sites from two patients. The morphology recurrence plots show distinct checker board patterns in the different sites indicating that the activation patterns have different levels of complexity, yet these patterns tend to be repeatable over the course of the recording. For Patient A, the highest recurrence percentage was 79%, which was found both near the superior vena cava and the left inferior PV. The right superior PV also had a high recurrence percentage of 77%. These sites can be easily identified in the figure as the sites with the most red, indicating high cross-correlation for the majority of the activations. The $CL_R$ of the left inferior PV (201 ms), however, was much shorter than those of the right superior PV (215 ms) or of the superior vena cava (246 ms). The patient has had freedom from AF during the 13 months following his AF ablation targeting antral PV isolation. For Patient B, the highest recurrence percentage (71%) and shortest $CL_R$ (231 ms) were found in the RA septum. The morphology recurrence plot for this site had the highest cross-correlation values near 1 compared to the other sites in both atria. Patient B had a recurrence of AF 9 months following ablation targeting PV isolation. FIG. 9 shows examples of morphology recurrence plots and electrograms with different recurrence percentages and CLs.

FIG. 10 illustrates a table which shows the mean and standard deviations of CL, recurrence percentage, and $CL_R$ for the 14 atrial sites as well as the distribution of the minimum CL and $CL_R$ sites and maximum recurrence percentage sites. The sites with the highest recurrence percentage had an average value of 83±17%, located in the RA in 5 patients and in the LA in 14 patients. The sites with the shortest CL had an average CL of 125±15 ms. The shortest CL sites were in the RA in 11 patients and in the LA in 8 patients. The sites with the shortest $CL_R$ had an average $CL_R$ of 230±91 ms. The shortest $CL_R$ sites were in the RA in 3 patients and in the LA in 16 patients. FIG. 7 displays schematically the differences at each site between the CL and $CL_R$ for one patient. The impulses for the left plots represent all activation times for each site. The impulses on the right represent only the activation times for the most common morphology for that site. The left inferior PV in this patient can be seen to clearly have the highest Rec % and the shortest $CL_R$.

There was a substantial decrease between the site of highest recurrence percentage and the second highest percentage (81.9±17.0% vs. 72.2±13.5%). Similarly, there was a substantial increase between the shortest $CL_R$ and the second shortest $CL_R$ (224±90 ms vs. 254±94 ms). The percent difference between the shortest $CL_R$ and the shortest $CL_R$ in the contralateral atrium was 35±7%. For maximum recurrence percentage and the maximum recurrence percentage in the contralateral atrium, the percent difference was 25±5%. Both of these were significantly greater than the corresponding percent difference for minimum CL which was 11±2% (p<0.02).

Reproducibility of recurrence percentage, $CL_R$, and CL was assessed using coronary sinus recordings taken 14.4±7.8 minutes apart. Intraclass correlation coefficients for recurrence percentage, $CL_R$, and CL were 0.91, 0.98, and 0.82, respectively. The average recurrence percentage for atrial flutter recordings was 91±12% which was significantly higher than the maximum recurrence percentages of AF patients (82±17%, p<0.05).

DF was highly correlated with the reciprocal of CL (R=0.75, p<0.0001). Regularity index was only weakly correlated with recurrence percentage (R=0.16, p=0.008). CFAEs had significantly lower Rec % than non-CFAEs (31±14% vs. 62±20%, p<0.0001).

With a median follow-up time of 13 months, 7 of the 19 patients had documented AF recurrences after a 3 month blanking period post-ablation. Four of 5 patients (80%) with sites of highest recurrence percentage located in the RA had AF recurrences while 3 of 14 patients (21.4%) with sites of highest recurrence percentage located in the LA had AF recurrences (hazard ratio=6.76; 95% confidence interval: 1.05 to 32.3; p=0.04). All three patients with sites of shortest $CL_R$ located in the RA had AF recurrences while 4 of 16 patients (25%) with sites of minimum $CL_R$ located in the LA had AF recurrences (hazard ratio=4.95; 95% confidence interval: 1.05 to 25; p=0.05). AF recurrences occurred in 3 of 11 (27.3%) and 4 of 8 (50%) patients with minimum CL located in the RA and LA, respectively (hazard ratio=1.45; 95% confidence interval: 0.31 to 6.72; p=0.63). When comparing PV and non-PV sites, 5 of 9 patients (55%) with sites of minimum $CL_R$ located in a non-PV site had AF recurrences while 2 of 10 patients (20%) with sites of minimum $CL_R$ located near the PV had AF recurrences (hazard ratio=3.3; 95% confidence interval: 0.6 to 16.1; p=0.16).

In another study, nine purpose-bred hounds weighing 25 to 35 kg were used. The rapid atrial pacing model for AF was performed similar to previously published techniques. (See Morillo C A, Klein G J, Jones D L, and Guiraudon C M. Chronic rapid atrial pacing. Structural, functional, and electrophysiological characteristics of a new model of sustained atrial fibrillation. Circulation 91: 1588-1595, 1995 Mar. 1, which is hereby incorporated by reference). Sterile surgery for pacemaker implantation was performed for each dog. Endocardial pacing leads were placed into the right atrial appendage (RAA). The pacemakers were programmed to pace at 600 bpm at four times the capture threshold. The dogs were paced for 2 to 3 weeks prior to the mapping studies. Six of the nine dogs had sustained AF after the cessation of the pacing period and were used for electrogram recording and analysis. This protocol conforms to the Guide for the Care and Use of Laboratory Animals published by the U.S. National Institutes of Health (NIH Publication No. 85-23, revised 1996) and was approved by the Animal Care and Use Committee of Northwestern University.

Open chest study was performed via a lateral thoracotomy using standard techniques. (See Orton E C. Thoracic wall. In: Textbook of Small Animal Surgery, edited by Slatter D. Philadelphia, Pa., USA: Saunders, 2003, p. 374-375, which is hereby incorporated by reference). Electrograms during AF were obtained using a 448 channel electrical mapping system (UnEmap, Auckland, New Zealand). A triangular-shaped high density plaque with 130 electrodes was sequentially positioned on the left atrial appendage (LAA), superior portion of the posterior left atrium (PLA1), mid portion of the posterior left atrium (PLA2), RAA, and the right atrial free wall (RAFW). At least four successive 10-second recordings were obtained in each position. The 130 electrodes were equally spaced at 2 mm and allowed 117 simultaneous bipolar electrograms to be obtained in each recording. The plaque covers approximately 2 cm² of area. Additional recordings were made in the PLA and LAA of 5 normal dogs during atrial pacing with a 200 ms cycle length.

A previously published "cycle length iteration" method (23) used to detect AF activation was modified to accommodate the fast AF activation rates seen in the canine rapid atrial pacing model. First, the electrograms were preprocessed with similar steps used by Botteron G W, and Smith J M, a technique for measurement of the extent of spatial organization of atrial activation during atrial fibrillation in the intact human heart, IEEE Trans Biomed Eng 42: 579-586, 1995, which is hereby incorporated by reference. This was done using 40 Hz high pass filtering (2nd order Butterworth), rectification, and 30 Hz low pass filtering (2nd order Butterworth). The peak of this rectified and filtered signal with highest magnitude was the first detected activation time. Next, all peaks occurring within a 40 ms blanking period before and after the first detected beat were excluded. This process of detecting the next largest peak, adding this activation to the set, and applying the blanking period was repeated until the mean and median CL converges within 5 ms of each other. All signal processing in this study was performed using custom software developed using MAT-LAB (Mathworks, Natick, Mass.).

Figure 11:
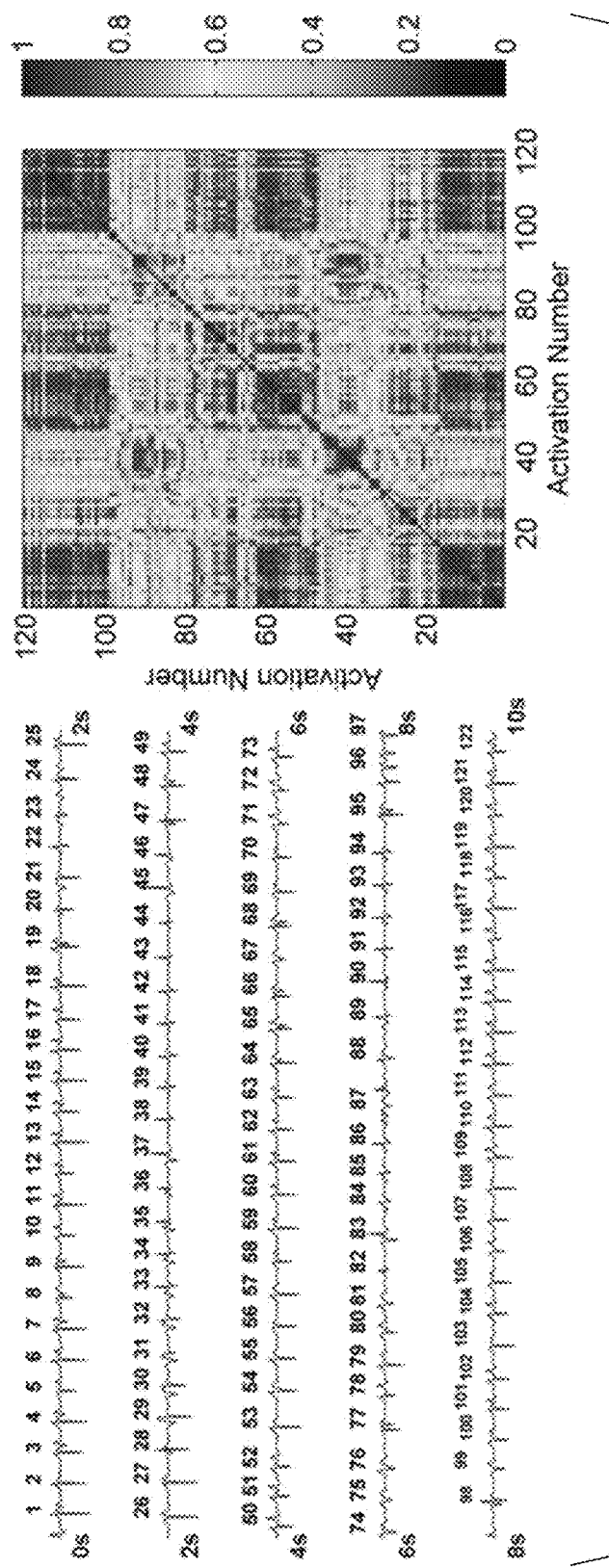
FIG. 11 shows an example of a 10-second AF electrogram recording with each detected activation numbered in chronological order.

Recurrence analysis originally described by Eckmann J-P, Oliffson Kamphorst S, and Ruelle D, Recurrence Plots of Dynamical Systems, Europhys Lett 4: 973-977, 1987, which is hereby incorporated by reference, was adapted for the purpose of studying electrogram morphology recurrence. Morphology recurrence analysis was performed using cross-correlation of 100 ms windows of each detected activation with every other activation in the recording. The maximum normalized cross-correlation value was determined for each combination of activations. The result was a set of N times N maximum cross-correlation values, where N is the number of activations. FIG. 11 shows an example of a 10-second AF electrogram recording with each detected activation numbered in chronological order. The morphology recurrence plot displays the cross-correlation values for every combination of activations. In one embodiment, this recurrence plot may be color-coded such that areas with a higher prevalence of one color correspond to electrograms with higher rates of morphology recurrences. This example shows periodic changes in morphology with alternating runs of waveforms with negative and positive deflections.

The most common morphology of a set of activations can be identified by finding the column on the morphology recurrence plot that has the most number of cross-correlation values above a user-defined value (0.8 was used in a previous clinical study). From this we quantified the rate of recurrence in two ways: 1) the percent of the activations that are represented by the most common morphology (Rec %) and 2) the mean cycle length separating activations with most recurrent morphology ($CL_R$). The $CL_R$ measure was designed to distinguish fast repeatable activity which may represent driver activity from slower repeatable activity that would more likely represent passive activation.

Activation directions for each electrode location and activation time were estimated by obtaining the activation times of the nearest neighbors within a 3×3 grid. If at least 6 electrodes in the 3×3 grid had activations within 15 ms of the activation time of the center location, a least-squares plane of best fit was determined using the activation times and the X-Y coordinates of the electrodes. The vector direction of the normal vector of the best fit plane was used as the activation direction. To quantify vector consistency, we calculated the activation vector index (AVI), defined as the percentage of activations for an electrode location that are within a 60 degree range that includes the most activations.

The activation markings were used to create animations of the AF activation patterns. To create the activation movies, triangular waveforms were used to replace the detected activations as a crude approximation of the shape of an atrial action potential. The onset of the waveform corresponds to the marked activation time. These animations were used to classify the captured activation patterns as having one of the following: (1) stable rotors; (2) passive activation consisting of single broad waterfronts traveling from one side of the plaque to the other side; and (3) chaotic activity that cannot be classified as having a rotor or passive activity.

Unpaired comparisons were made using Student's T test. Linear regression was used to test the association between AVI, Rec %, and CL measures. Intra-class correlation coefficient was used to test reproducibility of the measure over four successive recordings. A p-value <0.05 was considered statistically significant.

Figure 12:
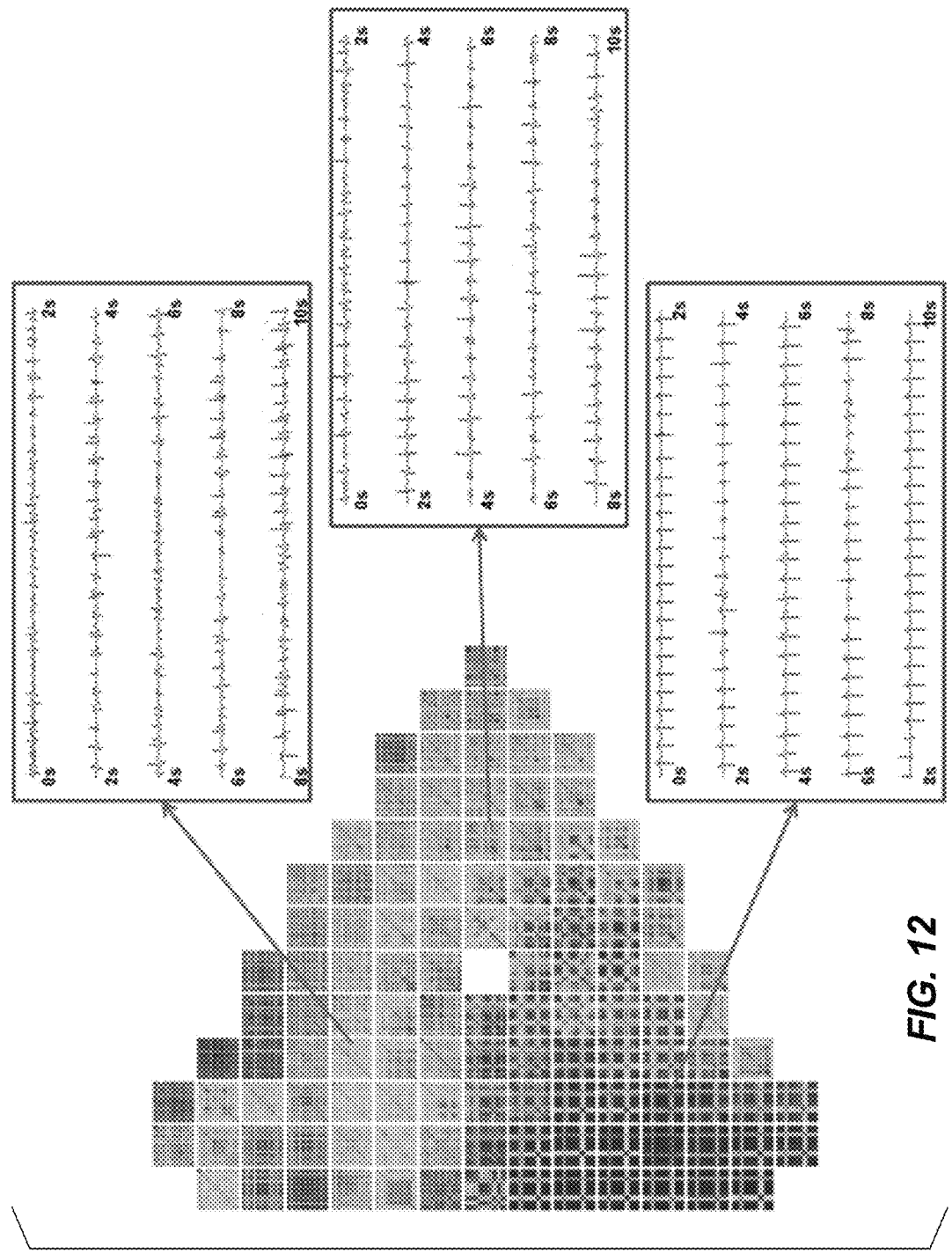
FIG. 12 shows an example of morphology recurrence plots for simultaneous recording sites arranged according to their relative location on a high density plaque.
Figure 13:
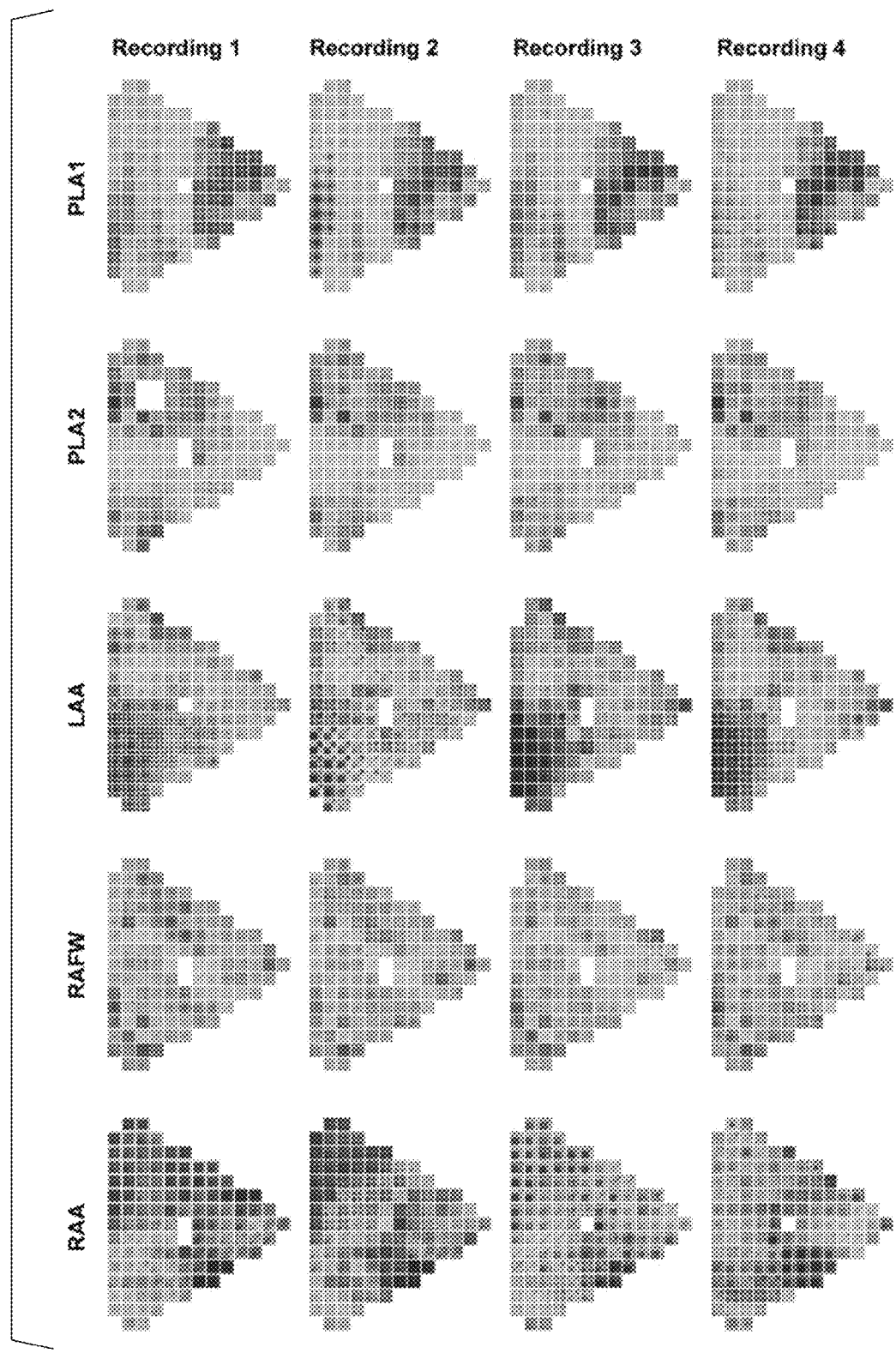
FIG. 13 shows an example of four consecutive sets of morphology recurrence plot maps from each of five sequentially recorded locations.

Qualitatively, the morphology recurrence plots were found to appropriately reflect morphology patterns of the electrograms, as well as show good reproducibility across multiple consecutive recordings. FIG. 12 shows an example of morphology recurrence plots for each of the simultaneous recording sites arranged according to their relative location on the high density plaque. The figure also shows three examples of the original electrograms of differing morphology complexity with arrows originating from the corresponding morphology recurrence plot. The morphology recurrence plot that has electrograms with a high degree of morphology consistency may be color coded in one color, whereas the two other plots having electrograms with more complex morphology patterns may be color coded in a different color. FIG. 13 shows an example of four consecutive morphology recurrence plot maps from each of the five sequentially recorded locations. Areas of the highest morphology recurrence have fairly stable locations across the four consecutive recordings.

Figure 15:
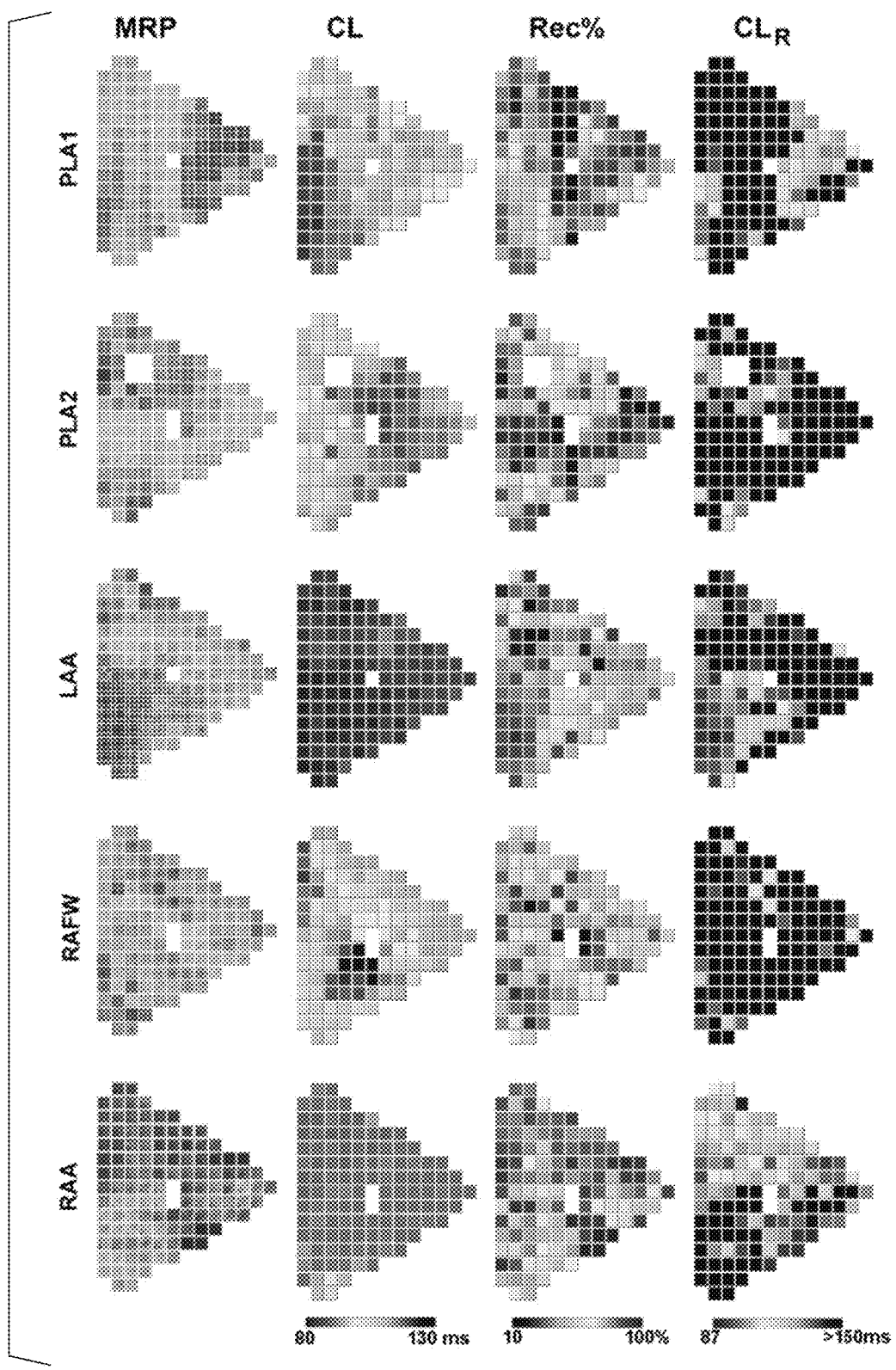
FIG. 15 shows the recurrence plot maps from one dog and the corresponding maps of CL, Rec %, and $CL_R$.

FIG. 14 illustrates tables (Table 1A, Table 1B, and Table 1C) which show the results for each of the six dogs at each of the five atrial sites. The shortest CL (Table 1A) was found in left atrium in the LA in four dogs and in the RA in two dogs. Rec % (Table 1B) was highest in LA in three dogs, highest in the RA in two dogs, and equal in the LA and RA one dog. The shortest $CL_R$ was found in the left atrium in five of the six dogs. FIG. 15 shows the recurrence plot maps from one dog and the corresponding maps of CL, Rec %, and $CL_R$. The figure illustrates how the areas of shortest $CL_R$ represent the areas that have a combination of high Rec % and short CL.

The shortest $CL_R$ was positivity correlated with both mean CL (R=0.85, p<0.0001) and minimum CL (R=0.87, p<0.0001), but not significantly correlated with mean Rec % (R=0.3, p=0.1) or maximum Rec % (R=0.03, p=0.89). Reproducibility over four consecutive recordings was observed with intra-class correlation coefficients of 0.98 (mean CL), 0.71 (minimum CL), 0.81 (mean Rec %), 0.81 (maximum Rec %), and 0.8 (minimum $CL_R$).

Figure 16:
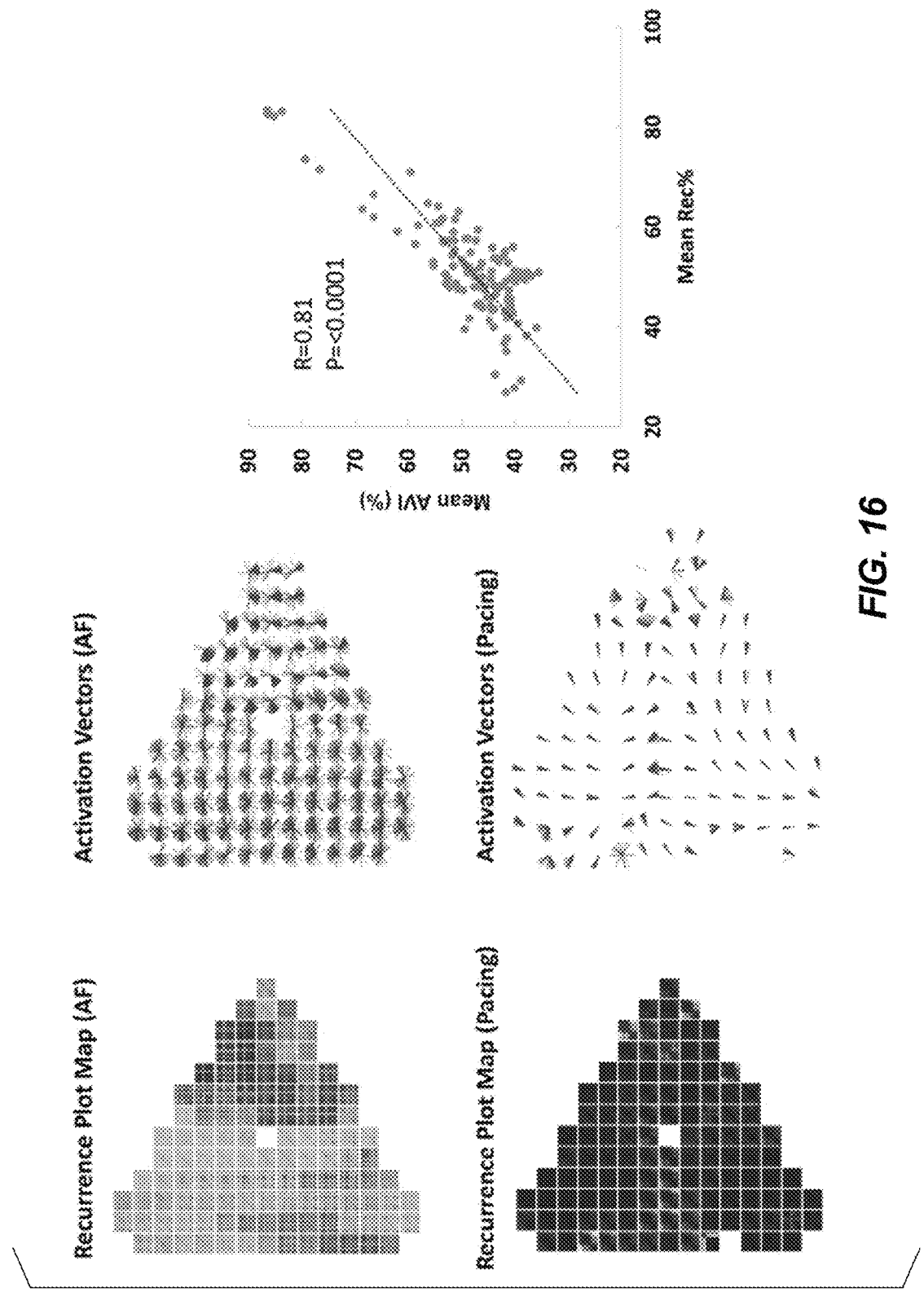
FIG. 16 shows differences in recurrence plot characteristics and activation direction consistency between AF and pacing conditions.

Analysis of activation vector consistency during AF showed AVI measurements (the percentage of activations within the optimal 60 degree range) with average values of 48±10% in PLA1, 46±7% in PLA2, 50±11% in the LAA, 51±13% in the RAA, and 48±10% in the RAFW. Electrograms recorded during 200 ms pacing in normal dogs showed both high Rec % and AVI values in PLA1 (99±1% and 97±2%, respectively), PLA2 (99±1% and 96±4%, respectively) and in the LAA (98±2% and 94±3%, respectively), as expected. The differences in recurrence plot characteristics and activation direction consistency between AF and pacing conditions are shown in FIG. 16. The upper recurrence plot map from a PLA recording site during AF shows a heterogeneous distribution of recurrence with the left side of the plaque showing patterns with less recurrence and the right side of the plaque showing highly recurrent activity. On the right of the recurrence plot map is a corresponding map showing the distribution of normalized activation vectors per electrode location. The left side of the plaque, where recurrence rates were lower, has vectors that appear to be radiating in a wide range of directions. In the right side of the plaque, where recurrence rates are higher, the activation vectors appear to be more concentrated in specific directions. In contrast, the lower recurrence plot map of electrograms recorded from the LAA in a separate animal during 200 ms pacing of the PLA show uniformly high rates of recurrence as expected. The normalized activation vectors for this recording also show very narrow ranges of vector directions. FIG. 16 (right most plot) also shows the high correlation between mean Rec % and mean AVI for all dogs and all sites during AF (R=0.81, p<0.0001).

Figure 17:
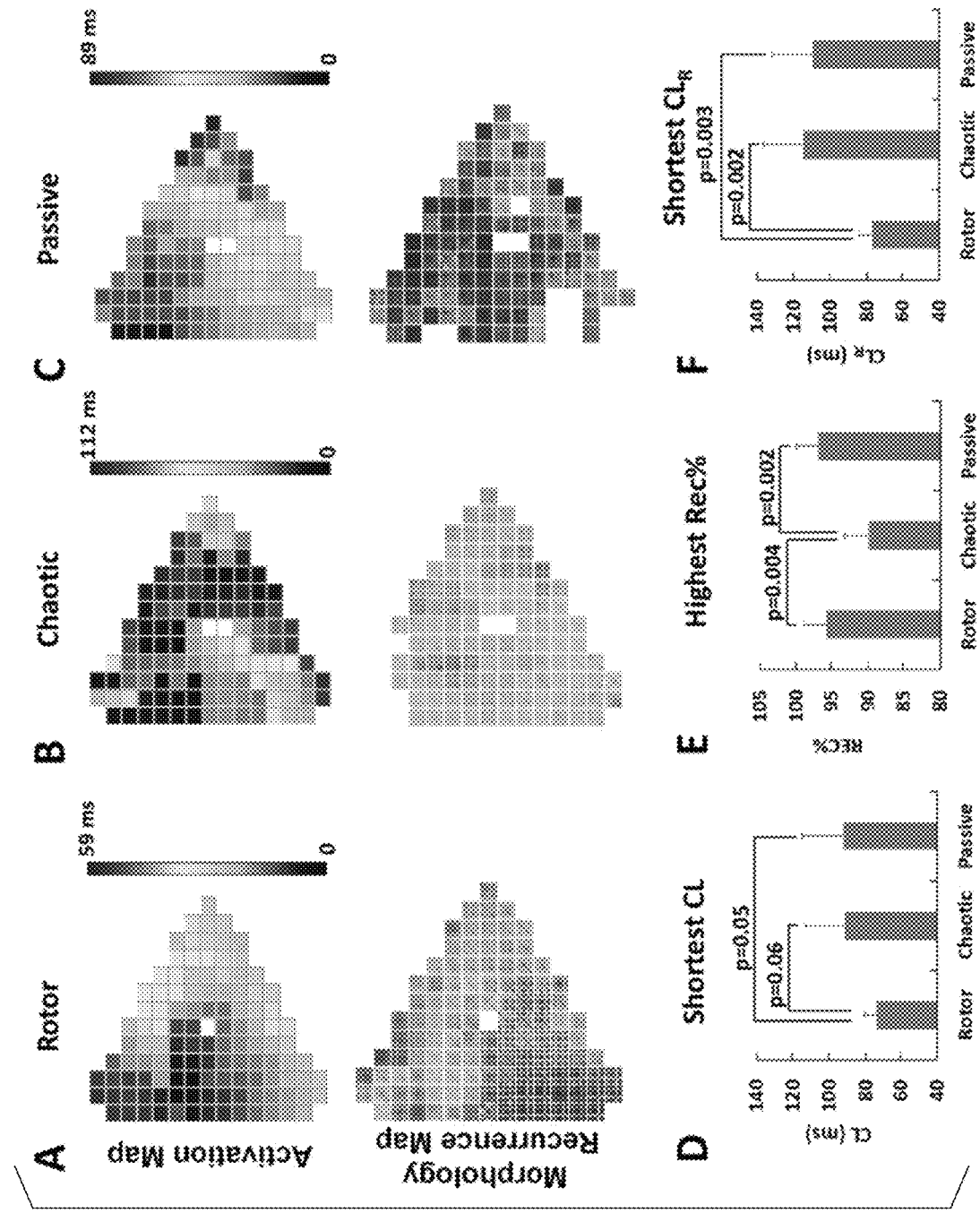
FIG. 17 shows examples of activation maps for three types of activity and the corresponding results of morphology recurrence plot analysis.

Activation animations of the AF recordings in the five sites of the six dogs were classified as either having stable rotors (N=3), chaotic activity (N=17), or passive activity (N=10). Examples of activation maps for each of the three types of activity are shown in FIG. 17, A-C. Rotors were located in the LAA in two dogs and in the RAA in one dog. FIG. 17, D shows that the minimum CL was shorter in locations with rotor activation (74±10 ms) than in those with chaotic (92±12 ms, p=0.06) and passive activation (91±14 ms, p=0.06). FIG. 17, E shows that sites with rotor (96±1%) and passive (97±3%) activation have significantly higher maximum Rec % than those with chaotic activation (90±7%, p=0.005). FIG. 17, F shows the locations with rotor activation (77±7 ms) had significantly shorter minimum $CL_R$ values than the locations with chaotic (115±22 ms, p=0.002) and passive activation (109±22 ms, p=0.003).

One or more embodiments of the disclosure may reduce one or more issues experienced by the current systems and methods for treating arrhythmia and atrial fibrillation by helping to determine the at least one location of interest for perpetuation or persistence of arrhythmia or atrial fibrillation. The surgeon may then perform a medical procedure on this at least one location of interest to reduce or eliminate the arrhythmia or atrial fibrillation.

The Abstract is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the disclosure is defined by the appended claims. Accordingly, the disclosure is not to be restricted except in light of the appended claims and their equivalents.

The invention claimed is:

1. A method of identifying at least one location of interest for perpetuation or persistence of arrhythmia or atrial fibrillation comprising:
   (a) recording electrograms at locations of at least one atrium of a subject;
   (b) selecting an electrogram recorded at one of the locations within the at least one atrium of the subject and extracting individual activations from the selected electrogram;
   (c) determining an electrogram repeatability values indicating repeatability of electrogram morphologies in the selected electrogram by comparing the individual activations extracted from the selected electrogram with a most common electrogram morphology in the selected electrogram;
   (d) repeating steps (b) and (c) for other electrograms recorded from other locations of the at least one atrium of the subject, thereby determining a plurality of electrogram repeatability values; and
   (e) identifying, amongst the locations of the at least one atrium, the at least one location of interest for perpetuation or persistence of the arrhythmia or the atrial fibrillation as that which has high electrogram repeatability based on preset parameters comprising: one of (1) exceeding a high repeatability threshold; (2) having a highest repeatability of the locations of the at least one atrium; or (3) having an electrogram repeatability value in a top preset number of repeatability values of the locations of the at least one atrium.

2. The method of claim 1 further comprising identifying the at least one location of interest for perpetuation or persistence of the arrhythmia or the atrial fibrillation as, amongst the locations of the at least one atrium, that which has the high electrogram repeatability based on the preset parameters, and which also has a short cycle length based on second preset parameters comprising: at least one of (4) a cycle length lower than a short cycle length threshold; (5) the location of the at least one atrium that has the high electrogram repeatability and a lowest cycle length; or (6) the location of the at least one atrium that has a cycle length that is in a shortest preset number of cycle length values.

3. The method of claim 2 comprising identifying the at least one location of interest for perpetuation or persistence of the arrhythmia or the atrial fibrillation as, amongst the locations of the at least one atrium, that which has the high electrogram repeatability based on the preset parameters, and which also has the short cycle length based on the second preset parameters comprising: (4) the cycle length lower than the short cycle length threshold.

4. The method of claim 2 comprising identifying the at least one location of interest for perpetuation or persistence of the arrhythmia or the atrial fibrillation as, amongst the locations of the at least one atrium, that which has the high electrogram repeatability based on the preset parameters, and which also has the short cycle length based on the second preset parameters comprising: (5) the location of the at least one atrium that has the high electrogram repeatability with the lowest cycle length.

5. The method of claim 2 comprising identifying the at least one location of interest for perpetuation or persistence of the arrhythmia or the atrial fibrillation as, amongst the locations of the at least one atrium, that which has the high electrogram repeatability based on the preset parameters, and which also has the short cycle length based on the second preset parameters comprising: (6) the location of the at least one atrium that has the cycle length that is in the shortest preset number of the cycle length values.

6. The method of claim 1 comprising identifying, amongst the locations of the at least one atrium, the at least one location of interest for perpetuation or persistence of the arrhythmia or the atrial fibrillation as that which has the high electrogram repeatability based on the preset parameters comprising: (1) exceeding the high repeatability threshold.

7. The method of claim 1 comprising identifying, amongst the locations of the at least one atrium, the at least one location of interest for perpetuation or persistence of the arrhythmia or the atrial fibrillation as that which has the high electrogram repeatability based on the preset parameters comprising: (2) having the highest repeatability of the locations of the at least one atrium.

8. The method of claim 1 comprising identifying, amongst the locations of the at least one atrium, the at least one location of interest for perpetuation or persistence of the arrhythmia or the atrial fibrillation as that which has the high electrogram repeatability based on the preset parameters comprising: (3) having the electrogram repeatability value in the top preset number of the repeatability values of the locations of the at least one atrium.

9. The method of claim 1 further comprising, for every atrium analyzed, generating an illustration showing the determined electrogram repeatability values at each of the locations.

10. The method of claim 1 wherein step (c) further comprises determining cycle lengths of the individual activations extracted from the selected electrogram.

11. The method of claim 10 further comprising for each atrium analyzed, generating an illustration showing the determined electrogram repeatability values at each of the locations, the generated illustration also showing the determined cycle lengths of high repeating electrogram morphologies at the locations.

12. The method of claim 1 further comprising performing a surgical or interventional procedure on the identified at least one location of interest to reduce or eliminate the arrhythmia or the atrial fibrillation.

13. A system for determining at least one location of interest for perpetuation or persistence of arrhythmia or atrial fibrillation comprising:
at least one electrogram device configured to record electrograms at locations within at least one atrium;
at least one processor in electronic communication with the at least one electrogram device; and
a memory in electronic communication with the at least one processor, wherein the memory comprises programming code for execution by the at least one processor, and the programming code is configured to determine electrogram repeatability values indicating repeatability of electrogram morphologies in a selected electrogram by:
(a) selecting an electrogram recorded at one of the locations within the at least one atrium;
(b) extracting individual activations from the selected electrogram;
(c) determining an electrogram repeatability value by comparing the individual activations extracted from the selected electrogram with a most common electrogram morphology in the selected electrogram;
(d) repeating steps (a), (b), and (c) for other electrograms recorded from other locations of the at least one atrium of the subject, thereby determining a plurality of electrogram repeatability values; and
the programming code is also configured to identify, amongst the locations of the at least one atrium, the at least one location of interest for perpetuation or persistence of the arrhythmia or the atrial fibrillation as that which has high electrogram repeatability based on preset parameters comprising: one of (1) exceeding a high repeatability threshold; (2) having a highest repeatability of the locations of the at least one atrium; or (3) having an electrogram repeatability value in a top preset number of repeatability values of the locations of the at least one atrium.

14. The system of claim 13 wherein the programming code is further configured to identify the at least one location of interest for perpetuation or persistence of the arrhythmia or the atrial fibrillation as, amongst the locations of the at least one atrium, that which has the high electrogram repeatability based on the preset parameters, and which also has a short cycle length based on second preset parameters comprising: at least one of (4) a cycle length lower than a short cycle length threshold; (5) the location of the at least one atrium that has the high electrogram repeatability and a lowest cycle length; or (6) the location of the at least one atrium that has a cycle length that is in a shortest preset number of cycle length values.

15. The system of claim 14 wherein the programming code is configured to identify the at least one location of interest for perpetuation or persistence of the arrhythmia or the atrial fibrillation as, amongst the locations of the at least one atrium, that which has the high electrogram repeatability based on the preset parameters, and which also has the short cycle length based on the second preset parameters comprising: (4) the cycle length lower than the short cycle length threshold.

16. The system of claim 14 wherein the programming code is configured to identify the at least one location of interest for perpetuation or persistence of the arrhythmia or the atrial fibrillation as, amongst the locations of the at least one atrium, that which has the high electrogram repeatability based on the preset parameters, and which also has the short cycle length based on the second preset parameters comprising: (5) the location of the at least one atrium that has the high electrogram repeatability with the lowest cycle length.

17. The system of claim 14 wherein the programming code is configured to identify the at least one location of interest for perpetuation or persistence of the arrhythmia or the atrial fibrillation as, amongst the locations of the at least one atrium, that which has the high electrogram repeatability based on the preset parameters, and which also has the short cycle length based on the second preset parameters comprising: (6) the location of the at least one atrium that has the cycle length which is in the shortest preset number of the cycle length values.

18. The system of claim 13 wherein the programming code is configured to identify, amongst the locations of the at least one atrium, the at least one location of interest for perpetuation or persistence of the arrhythmia or the atrial fibrillation as that which has the high electrogram repeatability based on the preset parameters comprising: (1) exceeding the high repeatability threshold.

19. The system of claim 13 wherein the programming code is configured to identify, amongst the locations of the at least one atrium, the at least one location of interest for perpetuation or persistence of the arrhythmia or the atrial fibrillation as location as that which has the high electrogram repeatability based on the preset parameters comprising: (2) having the highest repeatability of the locations of the at least one atrium.

20. The system of claim 13 wherein the programming code is configured to identify, amongst the locations of the at least one atrium, the at least one location of interest for perpetuation or persistence of the arrhythmia or the atrial fibrillation as that which has the high electrogram repeatability based on the preset parameters comprising: (3) having the electrogram repeatability value in the top preset number of the repeatability values of the locations of the at least one atrium.

21. The system of claim 13 further comprising a display, wherein the programming code is further configured to, for every atrium analyzed, generate an illustration on the display showing the determined electrogram repeatability values at each of the locations.

22. The system of claim 13 wherein the programming code is further configured to determine cycle lengths of the individual activations extracted from the selected electrogram.

23. The system of claim 22 further comprising a display, wherein the programming code is further configured to, for every atrium analyzed, generate an illustration on the display showing the determined electrogram repeatability values at each of the locations and to generate the illustration on the display to additionally show the determined cycle lengths of high repeating electrogram morphologies at the locations.

24. The system of claim 13 further comprising a surgical, treatment, or therapeutic device, wherein the programming code is configured to direct the surgical, treatment, or therapeutic device to the identified at least one location of interest to reduce or eliminate the arrhythmia or the atrial fibrillation.

* * * * *

UNITED STATES PATENT AND TRADEMARK OFFICE
CERTIFICATE OF CORRECTION

Page 1 of 1

PATENT NO. : 10,524,679 B2
APPLICATION NO. : 15/034296
DATED : January 7, 2020
INVENTOR(S) : Jason Ng et al.

It is certified that error appears in the above-identified patent and that said Letters Patent is hereby corrected as shown below:

In the Claims

Column 16, Claim 1, Line 1, "values" should be --value--.

Column 18, Claim 19, Line 53, "as location as that" should be --as that--.

Signed and Sealed this
Twenty-first Day of December, 2021

Drew Hirshfeld
*Performing the Functions and Duties of the
Under Secretary of Commerce for Intellectual Property and
Director of the United States Patent and Trademark Office*